United States Patent
Reith

(10) Patent No.: US 8,696,734 B2
(45) Date of Patent: Apr. 15, 2014

(54) RADIALLY EXPANDABLE SYSTEM FOR USE IN BODY TUBES

(75) Inventor: Walter Reith, Egenhofen (DE)

(73) Assignee: WRW Consulting GBR, Homburg (DE)

( * ) Notice: Subject to any disclaimer, the term of this patent is extended or adjusted under 35 U.S.C. 154(b) by 301 days.

(21) Appl. No.: 12/668,077

(22) PCT Filed: Jul. 4, 2008

(86) PCT No.: PCT/EP2008/005497
§ 371 (c)(1),
(2), (4) Date: Jan. 7, 2010

(87) PCT Pub. No.: WO2009/007070
PCT Pub. Date: Jan. 15, 2009

(65) Prior Publication Data
US 2010/0179640 A1    Jul. 15, 2010

(30) Foreign Application Priority Data
Jul. 7, 2007   (DE) .................. 10-2007-031-796

(51) Int. Cl.
*A61F 2/06*   (2013.01)
(52) U.S. Cl.
USPC ........................................ 623/1.15
(58) Field of Classification Search
USPC ............... 623/1.15, 1.34, 1.21, 1.4, 1.2, 1.11, 623/1.16, 1.36, 1.1; 604/104; 606/60, 194, 606/191, 198; 156/275.276, 275.7, 276; 977/724; 600/36
See application file for complete search history.

(56) References Cited

U.S. PATENT DOCUMENTS

| | | | |
|---|---|---|---|
| 5,100,429 A * | 3/1992 | Sinofsky et al. | 623/1.21 |
| 5,797,951 A | 8/1998 | Mueller | |
| 5,876,419 A * | 3/1999 | Carpenter et al. | 623/1.16 |
| 6,458,152 B1 * | 10/2002 | Khosravi et al. | 623/1.13 |
| 2002/0016626 A1 * | 2/2002 | DiMatteo et al. | 623/1.13 |
| 2002/0052650 A1 * | 5/2002 | Rourke et al. | 623/1.39 |
| 2003/0040791 A1 | 2/2003 | Oktay | |
| 2003/0093140 A1 | 5/2003 | Wall | |
| 2003/0135268 A1 | 7/2003 | Desai | |
| 2006/0122596 A1 * | 6/2006 | Dubrow | 606/60 |
| 2007/0255392 A1 | 11/2007 | Johnson | |
| 2009/0112305 A1 | 4/2009 | Goldmann et al. | |

FOREIGN PATENT DOCUMENTS

| | | |
|---|---|---|
| DE | 695 21 592 T2 | 6/1996 |
| DE | 10 2004 054 084 A1 | 5/2006 |
| DE | 10 2006 020 687 A1 | 2/2007 |
| EP | 0 604 022 A1 | 6/1994 |
| EP | 0 621 017 A1 | 10/1994 |
| EP | 0 716 836 B1 | 6/1996 |
| WO | 9421196 A2 | 9/1994 |
| WO | 9918890 A1 | 4/1999 |
| WO | 2005030095 A2 | 4/2005 |
| WO | 2006056981 A1 | 6/2006 |

* cited by examiner

*Primary Examiner* — Tuan V Nguyen
*Assistant Examiner* — Tin Nguyen
(74) *Attorney, Agent, or Firm* — Robert A. Blaha; Smith Risley Tempel Santos LLC

(57) ABSTRACT

A radially expandable system for the usage in body tubes is kept, by fixation of a first part and a second part relative to each other, in a second state in which the system exhibits a larger diameter compared to a first state. The fixation of the first part relative to the second part is performed by an adhesive. With the radially expandable system a body tube, for example a vein, can be assisted in its function. The first part and the second part can be arranged on or be formed by one single wall element or two different wall elements.

14 Claims, 15 Drawing Sheets

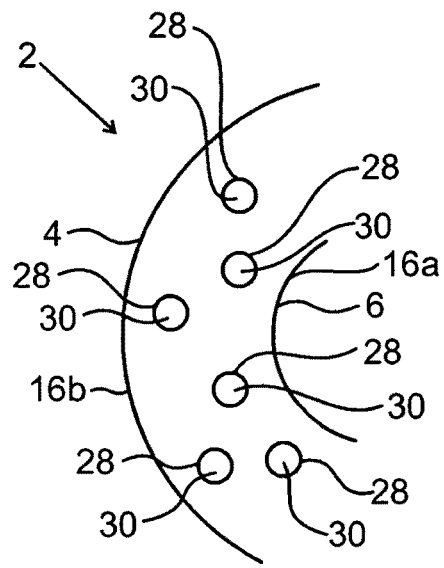
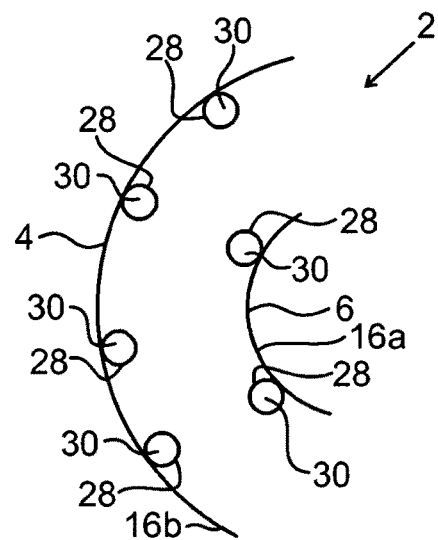
Fig. 3     Fig. 4
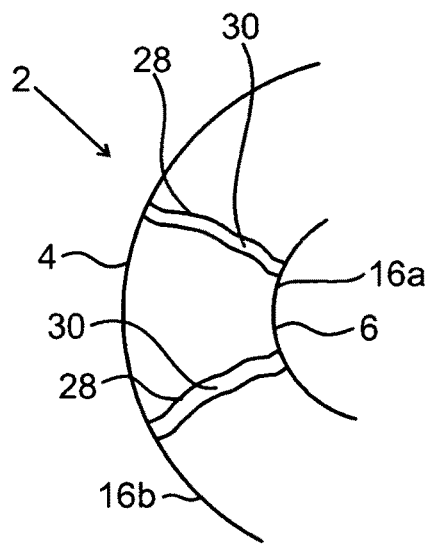
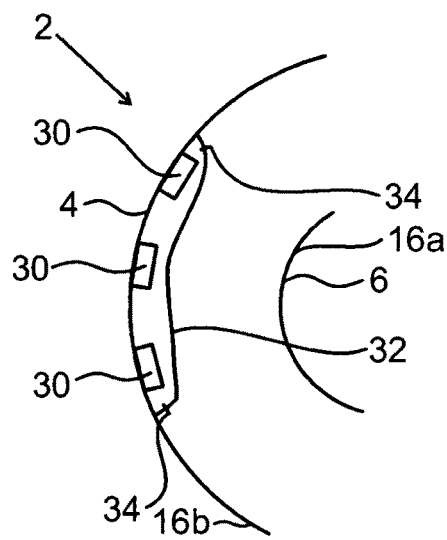
Fig. 5     Fig. 6

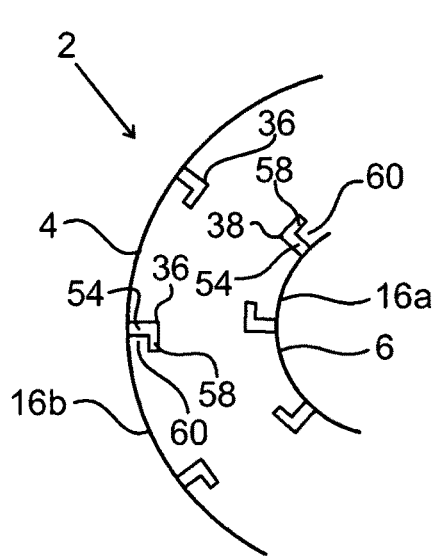
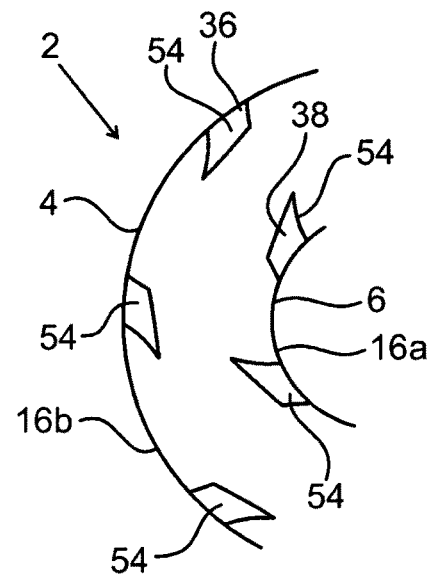
Fig. 17        Fig. 18
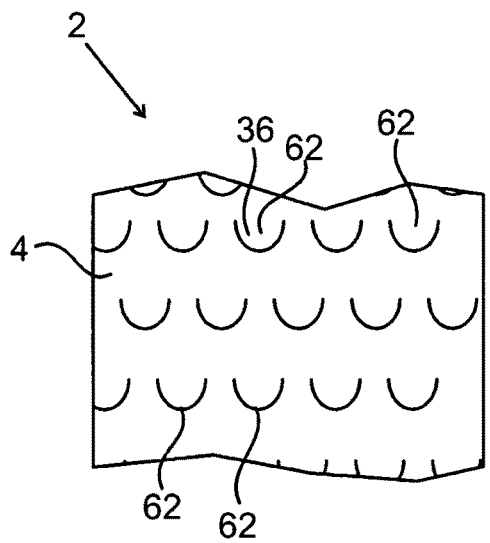
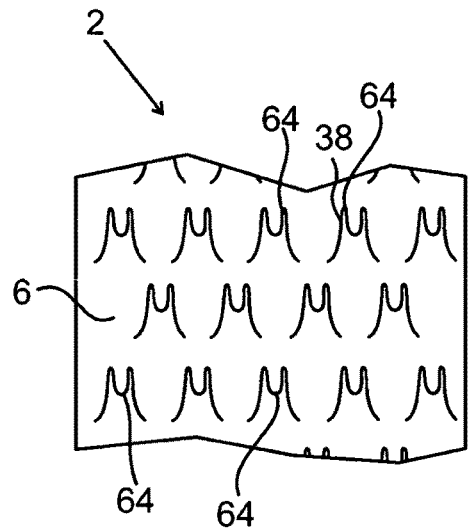
Fig. 19        Fig. 20

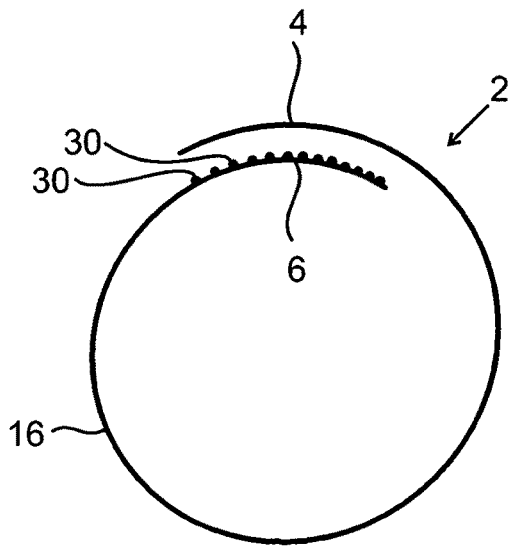
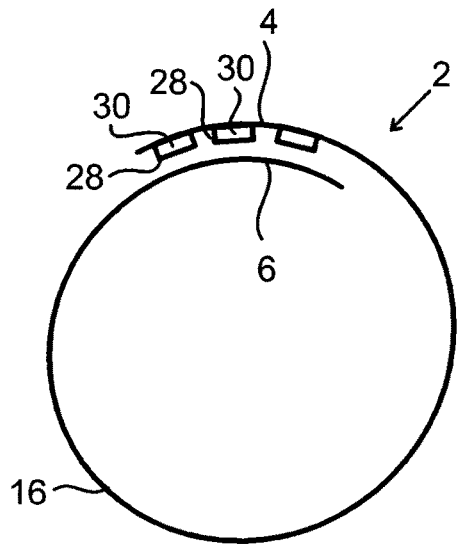
Fig. 24     Fig. 25
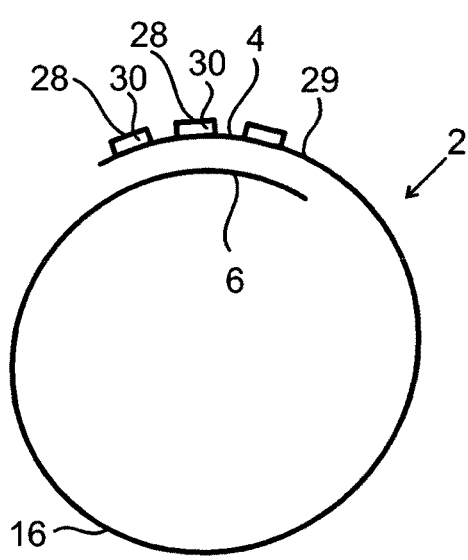
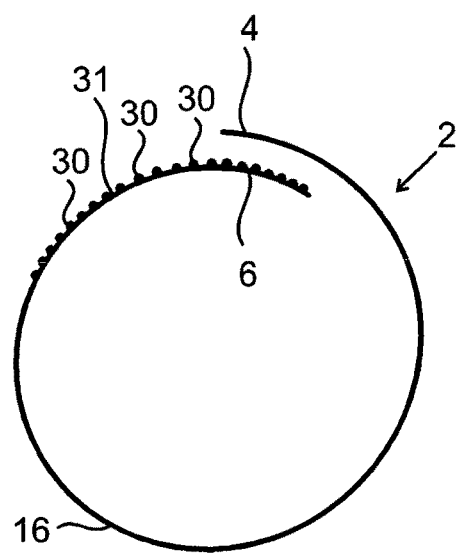
Fig. 26     Fig. 27

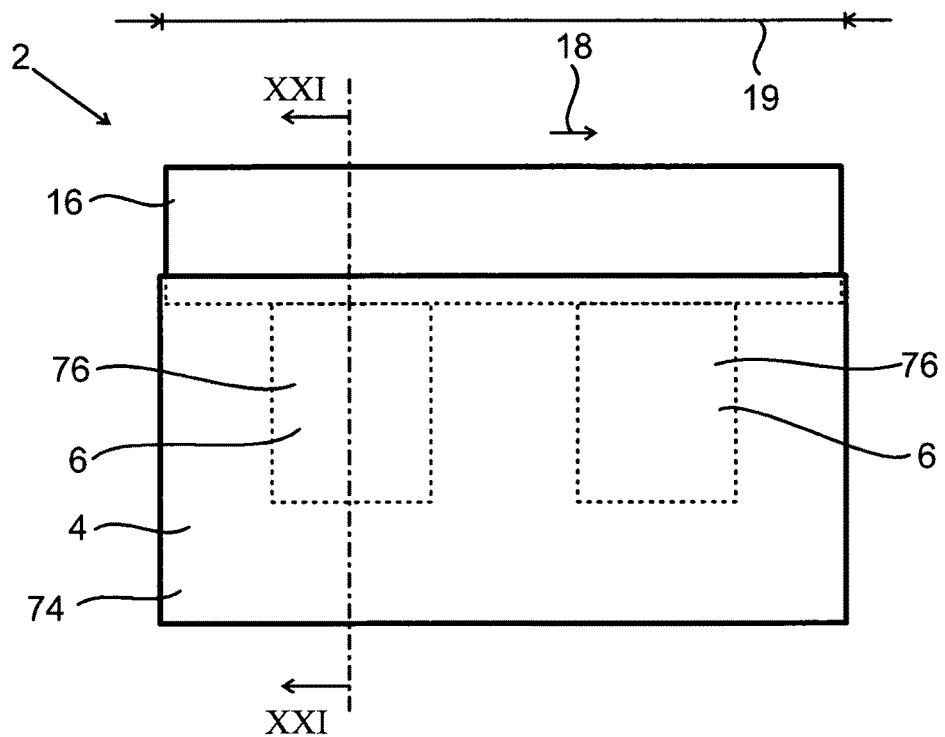
Fig. 32
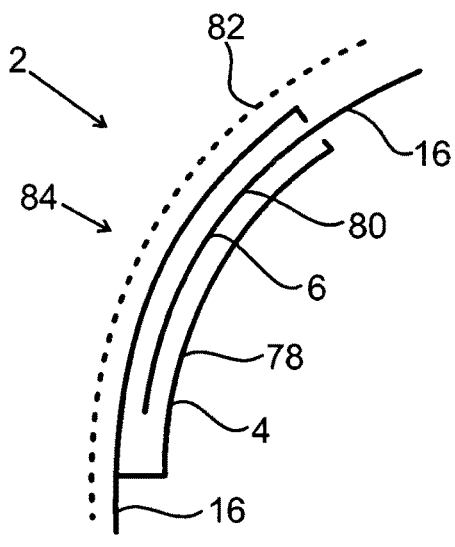 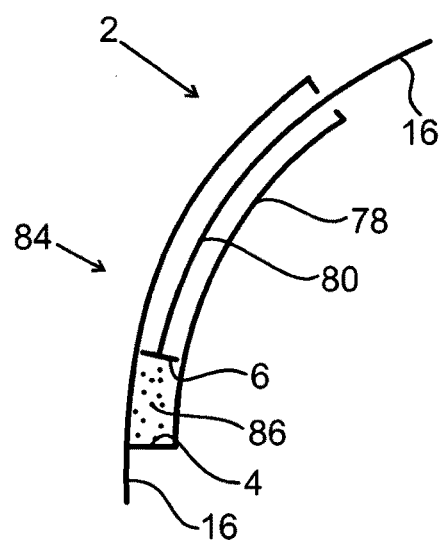
Fig. 33　　　　　　　　Fig. 34

RADIALLY EXPANDABLE SYSTEM FOR USE IN BODY TUBES

FIELD OF THE INVENTION

The present invention relates to the area of lining of body tubes of living creatures, e.g. man or animals. In particular, the invention relates to a radially expandable system for use in body tubes of living creatures.

BACKGROUND OF THE INVENTION

The German utility model G 9420887 U1 relates to a body for tube like channels to open, keep open, build or line tube like channels, i.e. arteries or veins.

In a first state the tube like body is elastic, for example due to incomplete polymerisation, and exhibits a small diameter. In a second state, the body shows the desired diameter and the desired stiffness and elasticity, defining an open cavity at least at one end. The second state is for example realised by irradiation with light. Furthermore G 9420887 U1 discloses the use of a memory shape alloy.

The irradiation of the body for its hardening/polymerisation is laborious, time-consuming and complicated in a vein. Linings with memory shape metals are expensive in production.

SUMMARY OF THE INVENTION

The invention is directed at different systems which can eliminate or at least alleviate the effects of at least part of the above mentioned problems. In particular, the invention relates to a system and a use according to the independent claims.

The herein described subject matter is based on the general idea of keeping a radially expandable system for lining of body tubes in a second state which exhibits a greater diameter compared to a first state. Keeping or maintaining the second state of the system can be done by fixation of two parts of the system which may in the second state face each other, i.e. lay opposite each other. The two parts may be fixed relative to each other or may be fixed to each other or may be fixed to the body tube.

According to a first aspect of the herein disclosed subject matter a radially expandable system for use in body tubes is provided having a first part and a second part and an adhesive. In a first state, the system has a first diameter. The system is bringable into a second state in which the system shows a second diameter which is larger than the first diameter. In the second state the first part and the second part are fixable relative to each other by means of the adhesive to keep the system in the second state. According to an illustrative embodiment, the first part and the second part, when being fixed relative to each other, form a structural part of the system i.e. they contribute to the structural integrity of the system in the body tube to thereby provide for assistance of the function of the body tube. According to another illustrative embodiment, the first part and the second part, when being fixed relative to each other, form a structural body of the system wherein the structural body provides for the structural integrity of the system in the body tube to thereby provide for assistance of the function of the body tube.

According to another illustrative embodiment, the first part and the second part are facing each other in the second state.

According to another illustrative embodiment, the adhesive is disposed for adhering together the first part and the second part in said second state.

According to still another illustrative embodiment, the adhesive is disposed on at least one of the first part and the second part.

According to still another illustrative embodiment, the adhesive is disposed in a reservoir.

According to still another illustrative embodiment, in the second state the reservoir is disposed in between the first part and the second part.

According to still another illustrative embodiment, the system further comprises, e.g. on at least one of the first part and the second part, an outer surface which is exposed in said second state. The adhesive is disposed on the outer surface for adhering said outer surface in said second state to the body tube to thereby fix the first part relative to the second part.

Herein, the term adhesive generally includes a physically curing adhesive, a chemically curing adhesive, or a non-curing adhesive. A non-curing adhesive may be an adhesive which provides adhering forces in the form of van-der-Waals forces. For example, without being limited hereto, a non-curing adhesive may include or consist of a plurality of fibers of suitable number and dimension which provide the desired adhering force. Such a non-curing adhesive is known to exist on the feet of Geckos.

For example, just to illustrate some possible combinations of the above mentioned embodiments, the adhesive may include a plurality of fibers which adhere on the body tube. According to another example, the van-der-Waals adhesive, e.g. in the form of adhering fibers, is provided on the first part or on the second part. According to still another example, both the first part and the second part comprise such fibers which exert van-der-Waals bonding forces to each other. According to other examples, the adhesive is a tissue adhesive, e.g. cyanoacrylate.

According to still another illustrative embodiment, the first part and/or the second part extends over part of a longitudinal extent of the system.

According to an illustrative embodiment of such a system, the first part exhibits a least one first fixation element; and the second part exhibits at least one second fixation element, wherein the at least one first fixation element and the at least one second fixation element mechanically fix together the first part and the second part in the second state.

According to another illustrative embodiment, the at least one first fixation element is arranged on a radially inner surface of the first part; and the at least one second fixation element is arranged on a radially outer surface of the second part.

According to still another illustrative embodiment, the second part is formed by at least one ear; and in the second state, the first part clasps the at least one ear from one side or, according to another illustrative embodiment, from two sides.

According to still another illustrative embodiment, the first part is formed by at least one pocket; and the ear of the second part is insertable into the pocket.

According to still another illustrative embodiment, the system comprises a spreader device which is activatable to move the first part and the second part relative to each other into the second state.

According to still another illustrative embodiment, the system comprises a spreader device which is activatable to keep the first part and the second part relative to each other in the second state.

According to still another illustrative embodiment, the spreader device comprises a foamable material or is formed from a foamable material.

According to still another illustrative embodiment, the system further comprises at least one marker being visible in an imaging method for imaging a body tube of humans or animals.

According to still another illustrative embodiment, the marker exhibits a configuration, which unambiguously defines its spatial orientation.

According to still another illustrative embodiment, the second part is arranged radially inside the first part.

According to still another illustrative embodiment, the system further contains a wall element which in the second state defines at least a part of a passage way extending in longitudinal direction of the system through the system.

According to still another illustrative embodiment, the wall element exhibits the first part and the second part.

According to still another illustrative embodiment, the wall element, which in the second state defines at least a part of a passage way extending in the longitudinal direction of the system through the system, exhibits the second part, and a further wall element exhibits the first part.

According to still another illustrative embodiment, the wall element which exhibits the second part is hose-like closed in peripheral direction or the further wall element which exhibits the first part is hose-like closed in peripheral direction.

According to still another illustrative embodiment, the wall element which exhibits the second part as well as the further wall element which exhibits the first part are both hose-like closed in peripheral direction and the further wall element which exhibits the first part is arranged radially outside the wall element which exhibits the second part.

According to still another illustrative embodiment, the system exhibits at least one lateral opening to the passage way which extends in longitudinal direction through the system.

According to still another illustrative embodiment, the system is cylindrical with a constant outer diameter in longitudinal direction of the system.

According to still another illustrative embodiment, the system exhibits an outer diameter varying in longitudinal direction.

According to still another illustrative embodiment, the system is a body-tube insert.

Further embodiments are defined by combination of two or more of the above mentioned illustrative embodiments, examples, and the embodiments described in the detailed description section. It should in particular be understood that the above mentioned fixation elements and/or spreader devices may keep the system in the second state until the adhesive (in the form of curable adhesive in this embodiment) has cured. Moreover, the fixation elements and/or spreader devices may be combined with the adhesive just to combine the adhering and mechanical holding forces so as to achieve a desired resistance of the system against leaving the second state. The embodiments of the herein disclosed subject matter will become apparent with the following detailed description referring to the attached drawings. In the drawings, mechanical fixation measures and adhesive fixation measures are shown separately throughout several drawings. However, it should be understood, that the individual measures may be combined in accordance with the claimed subject matter.

In the following, exemplary embodiments are described with reference to the drawings. In drawings, lines provided with roman numbers, e.g. XI-XI, indicate a respective section view of the given number, i.e. FIG. 11 in this example.

BRIEF DESCRIPTION OF THE DRAWINGS

FIG. 1 to FIG. 46 show radially expandable systems according to illustrative embodiments described herein.

DETAILED DESCRIPTION

Figure 1:
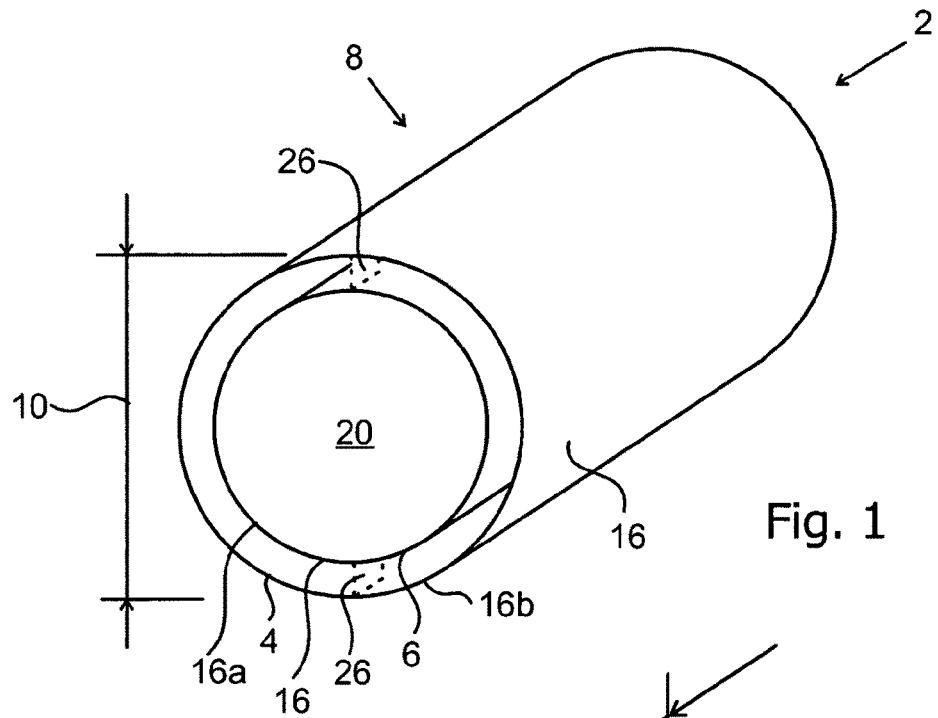

While the subject matter disclosed herein is described with reference to the embodiments as illustrated in the following detailed description as well as in the drawings, it should be understood that the following detailed description as well as the drawings are not intended to limit the present invention to the particular illustrative embodiments disclosed. Rather, the described illustrative embodiments merely exemplify the various aspects of the present invention, the scope of which is defined by the appended claims.

The presentation of the drawings is schematic. In the various figures similar or identical elements are provided with the same reference signs, or with reference signs which differ only in the first character.

The drawings show embodiments of a radially expandable system, in particular of a lining for a body tube, for use in body tubes of creatures. In this sense, a body tube can for example be an artery, a vein, or any other tube-like system of a creature, for example a urethra, gall tube or trachea. The term "creature" includes in particular humans and animals.

In general, the system can be used for function support and repair, respectively, of a body tube in which the system is placed. For instance, the system can be used to repair body tubes which are narrowed or blocked. Moreover, the system can be used to repair aneurysm.

Figure 2:
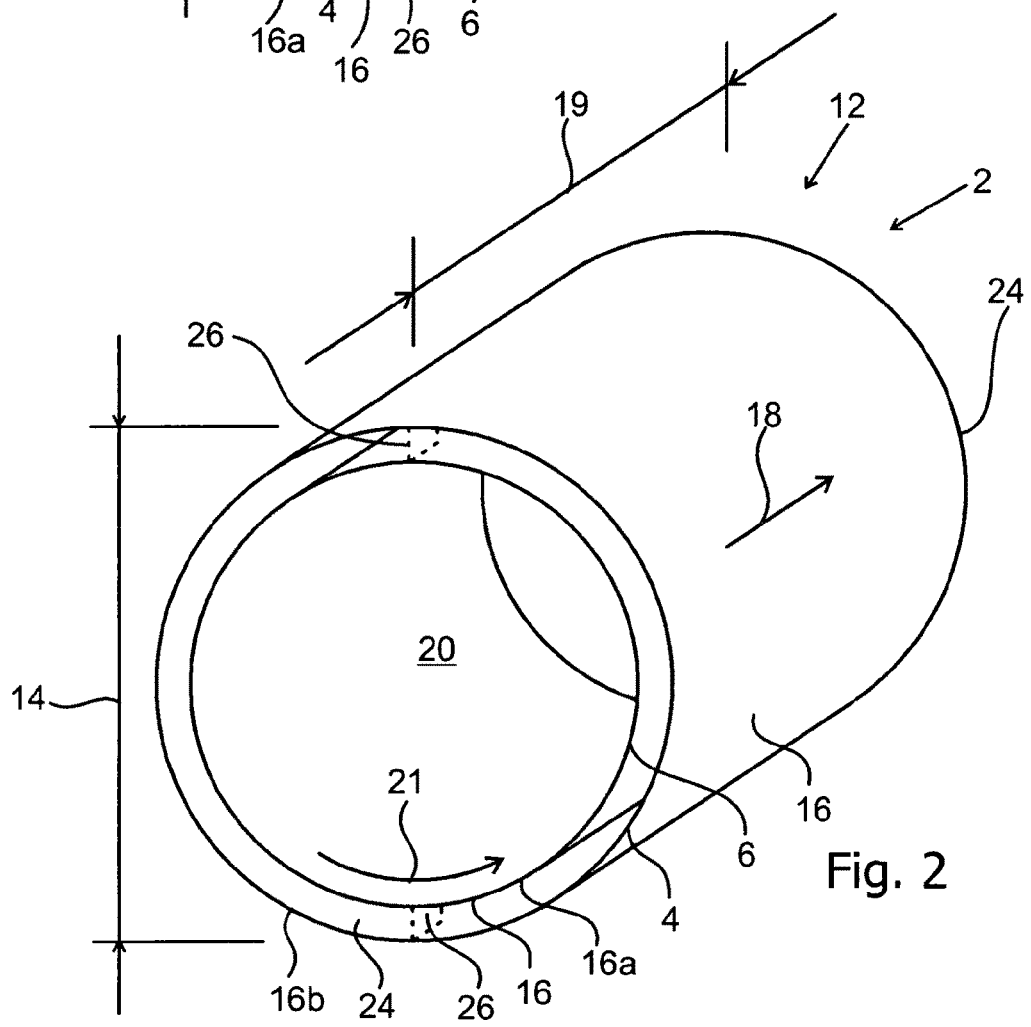

FIG. 1 and FIG. 2 display a radially expandable system 2 according to illustrative embodiments of the herein disclosed subject matter. System 2 generally comprises a first part 4 and a second part 6, wherein the system 2 exhibits in a first state 8 (FIG. 1) a first diameter 10. The system 2 is configured to be bringable, e.g. to be transferable to a second state 12 (FIG. 2), in which the system 2 has a second diameter 14, which is larger than the first diameter 10. Furthermore, the system 2 is configured such that in the second state 12 the first part 4 and the second part 6 are facing each other and are fixable relative to each other to keep the system 2 in the second state. For example the system may be configured such that in a second state 12 the first part 4 and the second part 6 are facing each other and are fixable to each other. As it is apparent from FIG. 1, according to an illustrative embodiment, the first part 4 and the second part 6 may be facing each other already in the first state. According to an illustrative embodiment, the second state is a predetermined state with a predetermined second diameter. According to a further embodiment, the diameter 14 of the second state 12 is variable. For instance, the second state 12 may be adjustable before, during or after the insertion of the system into the body tube.

With a system 2 according to illustrative embodiments of the herein disclosed subject matter it is possible to open permanently and/or keep open a narrowed or closed body tube. Furthermore according to one embodiment it is possible, in case of tissue weakness of a body tube which has let to an aneurysm or may lead to an aneurysm, to bridge the section of the body tube featuring the tissue weakness. In this way the build-up of an aneurysm can be avoided or the enlargement of an existing aneurysm can be prevented.

According to an illustrative embodiment, the radially expandable system 2 comprises a wall element 16a which defines in the second state 12 at least part of a passage way 20 extending in longitudinal direction 18 of system 2 through system 2, as exemplarily depicted in FIG. 2.

An expansion of the system can for example be done by balloon dilatation. At this, a balloon is placed in the passage way 20 and the radially expandable system 2 is brought into the second state 12 by blowing up the balloon. Furthermore the expansion can be carried out by pressing in liquids in channels. Further, the expansion can be done pure mechanically, for example by use of a material which changes its shape by impact of temperature, for example a bimetal or a shape memory alloy like nickel titanium (NiTi). The diameter of system 2 in the second state can be variable. That is to say that one size of the radially expandable system can be inserted in miscellaneous body tubes or in body tubes of different diameters. For instance, with one single size of system 2, different body tubes can be extended. Using pure mechanical fixation/interlocking, expansion can later be performed at necessity one or more times, for example in the course of an intervention in which the system in placed in the body tube, or at a further intervention, for instance after several months or years.

According to a further embodiment, in the second state 12 the system 2 is tube like or hose like. According to a further embodiment, the cross section of system 2 is circular. The passage way 20 enables the transfer of liquids or gases according to the respective function of the body tube in which the system 2 is inserted.

According to an embodiment, the wall element 16a exhibits the second part 6 and a further wall element 16b, which is arranged radially outside the wall element 16a, exhibits the first part 4. According to a further embodiment both wall elements 16a and 16b are hose-like closed in peripheral direction as shown in FIG. 1 and FIG. 2. According to a further embodiment, at least one of the wall elements 16a, 16b is open, i.e. not hose like closed, in peripheral direction.

Herein, reference number 16 denominates generally a wall element, whereas individual wall elements out of at least two wall elements of a system 2 are indicated by the reference numbers 16a, 16b, 16c, etc.

According to a further embodiment, the system 2 contains more than two wall elements 16. According to a still further embodiment, the system 2 contains only one single wall element 16. According to a further embodiment, the system 2 contains two or more wall elements 16 which extend in a peripheral direction over a certain circumferential section and add in the second state to a system which is hose-like closed in peripheral direction.

In system 2 shown in FIG. 1 and FIG. 2, both wall elements 16a and 16b are deformable, whereby the system 2 can be brought into the second state.

According to an embodiment, in order to allow the system 2 to reach the second state, at least one wall element of the system 2, for example the wall elements 16a and 16b are elastically deformable. According to a further embodiment, the deformation of at least one wall element 16a, 16b is partially plastic.

Fixing the first part 4 and the second part 6 together can be done in any appropriate way in accordance with the claimed subject matter. According to an embodiment, an adhesive is provided in order to fix the first part and the second part relative to each other. For example, the first part and the second part can be chemically fixable to each other, for instance glueable to each other. For example a placement of an adhesive between the first part 4 and the second part 6 can take place straight before an intervention in which the system 2 is placed in the body tubes of a patient. Furthermore the placement of the adhesive between the first part 4 and the second part 6 can take place during the intervention in which the system 2 is placed in one of the body tubes of a patient. In both of the two last-mentioned examples, the system 2 can be distributed in a status without adhesive.

According to an embodiment depicted in FIG. 1 and FIG. 2, the system 2 is open in-between the first part 4 and the second part 6 on both front sides. In this case connecting elements 26 (shown dashed in FIG. 1 and FIG. 2) between the first part 4 and the second part 6 may be provided to avoid uncontrolled slipping of the first part 4 and the second part 6 against each other. According to other embodiments, uncontrolled slipping of the first part 4 and the second part 6 can be avoided in other ways, for instance by an appropriate feed-in device.

According to a further illustrative embodiment, the system can at least in the first state be closed on at least one front side, for example by at least one front-side closure. For instance the system can be closed at one single front side 24. Further the system can be closed at two front sides. The closing or the front side interlocking, respectively, can be done in any suitable way, for example by adhering, welding or sewing.

According to a further embodiment, the system 2 is constructed to provide, at the expansion of system 2, contact between a tissue adhesive enclosed in the system 2 and a body fluid. For instance the front-side closure can be constructed to rip during the expansion. According to a further illustrative embodiment, the system 2 can be constructed to become permeable for body fluids in the second state. For example the front side closure and/or the wall of herein described systems 2 can be constructed to have in the second state breakthroughs, for example in form of pores which are permeable for body fluids.

According to an embodiment of the herein disclosed subject matter an adhesive reservoir, e.g. a glue reservoir can be disposed between the first part and the second part.

According to an embodiment, the system 2 is closed between the first part 4 and the second part 6 on at least one front side (not shown). In this case, a space in between the first part 4 and the second part 6 can be used as adhesive reservoir.

FIG. 3 shows a cross-sectional view of a system 2 according to illustrative embodiments of the herein described subject matter. According to an embodiment of the herein disclosed subject matter, at least one separate adhesive/glue reservoir 28 is placed between the first part 4 and the second part 6, the adhesive reservoir containing an adhesive 30 for fixing the first part 4 and the second part 6 to each other. The separate adhesive reservoir 28 may be formed by a closed spherical envelope in which is enclosed an adhesive 30. For example, the separate adhesive reservoir 28 may be built by adhesive containing bubbles. According to other embodiments, the at least one separate adhesive reservoir can have any other form. The at least one separate adhesive reservoir 28 can be free to move between the first part 4 and the second part 6 as shown in FIG. 3. According to other embodiments the at least one separate adhesive reservoir 28 is fixed to the first part and/or the second part as is exemplarily shown in FIG. 4.

According to a further embodiment of a system 2 the adhesive reservoir 28 extends between the first part 4 and the second part 6 and is fixed to the first part 4 as well as to the second part 6 as shown in FIG. 5. According to a further embodiment the at least one separate adhesive reservoir 28 acts additional as connecting element which fixes the first part 4 and the second part 6 against each other corresponding to the function of the connecting element 26 of the embodiment shown in FIG. 1 and FIG. 2.

According to an embodiment of the herein disclosed subject matter, the at least one separate adhesive reservoir 28 is made of a non elastic material or a material with low elasticity so that the separate adhesive reservoir 28 rips during the expansion of the system 2 into the second state and releases the adhesive 30. According to a further embodiment the at least one separate adhesive reservoir is opened by external impact to release the covered adhesive 30 and to fix the first part 4 and the second part 6 together. An external impact comprises for example contact free energy like for example a laser beam or ultrasound, or mechanical impact like for example a sharp device.

According to a further embodiment of the herein disclosed subject matter, on at least on one of the first part 4 and the second part 6 an adhesive 30 is located. For instance an adhesive 30 may be located on the second part 6 as shown in FIG. 6. For example, the adhesive 30 can be applied directly on the first part 4 or on the second part 6. The application of the adhesive can be on the entire surface, on part of the surface and/or in the form of certain structures. In case the adhesive 30 is applied in certain structures, these can be predetermined in some embodiments by a surface structure on the surface of the cover membrane. The surface structure can for example be predetermined by imprinting. For instance the surface structure can exhibit cavities which selectively can be filled up by use of a doctor blade, whereby the respective adhesive structure is created.

When curable adhesive is used, the adhesive structures can be chosen in a way that after curing of the adhesive in the second state, elasticity and/or mechanical stability of the system 2 reaches certain values. Through appropriate trials or simulations, the adhesive structures can be optimized to achieve maximal values for elasticity and/or mechanical stability of the system 2 in the second state.

In the first state 8 of the system 2, the contact of the adhesive 30 with blood and body fluids can be prohibited by a cover 32 which is arranged over the adhesive. The cover 32 is essential for utilization of a tissue adhesive, however it can be used together with other adhesives.

The adhesive can be released in different ways from the cover 32. For example the cover can be designed and/or arranged so that it rips and/or gets porous during expansion. According to a further embodiment, the cover of the adhesive exhibits a tear-off element 34, for example a tear-off filament. For example the tear-off element 34 can create a crack or gap in the cover 32 through which the adhesive 30 leaks to adhere the first part 4 with the cover and the second part 6. Further the tear off-element 34 can be strap like so that the adhesive 30 is laid open laminar to adhere the first part 4 and the second part 6 directly together.

After correct positioning of the system in the body tube, the tear off element 34 can be operated by an appropriate device on the insertion system, for instance a catheter, to rip the cover whereby the adhesive comes out and hardens. This enables an accurate and controlled fixation of the system. In particular, the position of the adhesive seam is exact and in advance settable; further the point of time for ripping open can be chosen arbitrarily. The action of fixation (sticking or adhering together) is uncoupled from the action of expansion. After the expansion, the correct fit of the system 2 is controlled and not till then the tear element 34 is activated. Also there can be several covers 32 with adhesive located on the system 2, which can be ripped either simultaneously or separately, for example temporally shifted. In the different covers 32 there can be different adhesives.

For the "adhesive 30" any appropriate adhesive can be used, including physically curing, chemically curing or non-curing adhesives. Non-curing adhesives include substances which exert van-der-Walls forces to the adhering surfaces.

The use of curable adhesive has the advantage that the system cannot accidentally be brought again into the first state, e.g. by a hit against the body portion in the vicinity of the placed system 2. By usage of certain adhesives 30, the hardening time can be adjusted. An example for an appropriate adhesive 30 is for instance a one component adhesive which directly adheres together the first part 4 and the second part 6. A further example of an appropriate adhesive 30 is a reactive one component adhesive, for instance a tissue adhesive, which reacts with at least one constituent of the blood or of a body liquid as second component and thereby adheres the first part 4 with the second part 6. By usage of a tissue adhesive, the fast hardening of the adhesive is realizable. By choosing an appropriate tissue adhesive the hardening time is adjustable to a desired value. A further example of an appropriate adhesive 30 is a multi component adhesive which at least two components can for instance be located in different adhesive reservoirs 28. On opening of the adhesive reservoirs 28 the at least two components are released, react with one another and thereby glue the first part 4 with the second part 6. The adhesive, for example the reactive one component adhesive or the multi component adhesive, can be foamy or non foamy. With a foamy adhesive, during the reaction of two or more components a foam is formed which leads to a volume increase. This volume increase can be used for an expansion, i.e. for the creation of the second state, alone or among other means.

Figure 7:
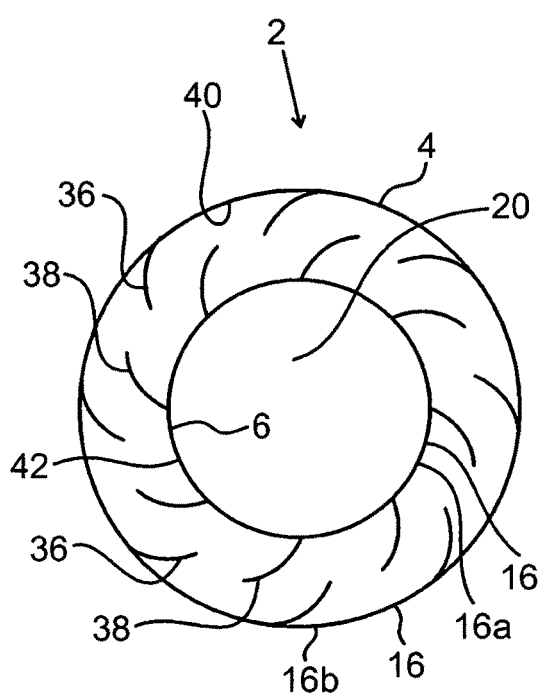

Besides an adhering fixation (including van-der-Waals fixation) or a chemical fixation, the fixation can also take place mechanically. FIG. 7 shows a system 2 according to illustrative embodiments of the herein disclosed subject matter. According to a illustrative embodiment, the first part 4 exhibits at least one first fixation element 36 and the second part 6 exhibits at least one second fixation element 38. The at least one first fixation element 36 and the at least one second fixation element 38 fix the first part 4 and the second part 6 in the second state 12 to each other. For instance a plurality of first fixation elements 36 and a plurality of second fixation elements 38 may be provided. The first fixation element 36 and/or the second fixation element 38 may comprise or consist of at least one hook. The first and the second fixation elements 36, 38 may be formed by hooks directed inclined against each other. The hooks directed against each other slide along each other during expansion, however get caught with a movement in a direction towards the first state, i.e. with a reduction of the diameter of system 2, thereby fixing the first part and the second part together. In a illustrative embodiment in which the first part 4 is arranged radially outside the second part, the first and the second fixation elements in form of hooks 36 are located on a radially inner surface 40 of the first part 4 and on a radially outer surface 42 of the second part 6, i.e. the hooks 36, 38 are located on surfaces 40, 42 of the first part 4 and the second part 6 facing one another.

According to a further illustrative embodiment, the system shows two or more wall elements 16 each of which exhibits a first part 4 and a second part 6. In each case a first part 4 and a second part 6 are facing each other in the second state 12 and are fixable to each other.

Figure 8:
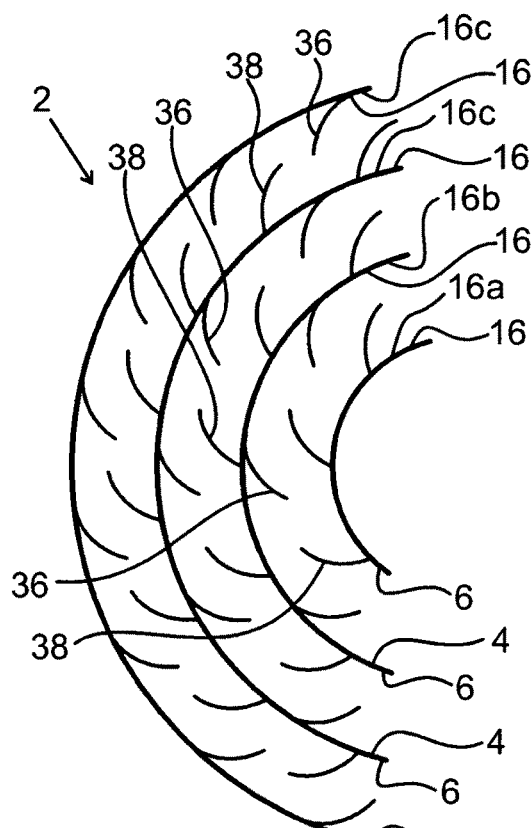

FIG. 8 shows a system 2 according to further illustrative embodiments of the herein disclosed subject matter. According to an embodiment, the system 2 exhibits two wall elements 16*a*, 16*b*, of which a first wall element 16*a* comprises or consists of the first part 4 and a second wall element 16*b* comprises or consists of the second part 6. According to a further embodiment the first wall element 16*a* exhibits, besides the first part 4, a second part 6 which overlaps in the second state 12 with a further first part 4 of a further wall element 16c and can be fixed relative to it, for example can be fixed to it. The further wall element 16c may exhibit besides the first part 4 also a second part 6 which overlaps in the second state 12 with a first part 4 of a further second wall element 16c. In other words according to an illustrative embodiment, there can be in between a radially outer wall element 16c and a radially inner wall element 16b one or more intermediate wall elements 16, whereby these intermediate wall elements 16 exhibit a first part 4 as well as a second part 6, in order to face a respectively further part 6, 4 of the radially outer wall element 16c and the radially inner wall element 16b in the second state 12, whereby in each case first parts 4 and second parts 6 each other can be fixed to each other. According to an illustrative embodiment, the wall elements 16a, 16b 16c are hose-like closed in peripheral direction and are positioned radially into each other.

Figure 9:
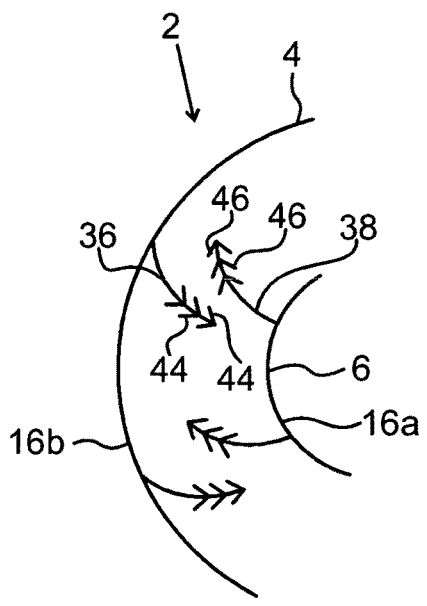

FIG. 9 shows a partial view of a system 2 according to illustrative embodiments of the herein disclosed subject matter. The system 2 as shown in FIG. 9 differs from the system 2 as shown in FIG. 7 in that on at least part of the hooks 36, 38 is disposed at least one barbed hook 44, 46. Each of the barbed hooks 44, 46 points in direction of the part 4, 6 on which their carrying hook 36, 38 is located. The barbed hooks can be attached evenly opposite each other, offset, or irregular.

Figure 10:
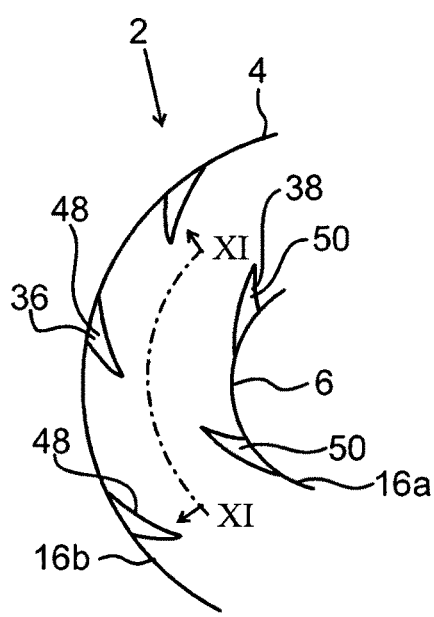
Figure 11:
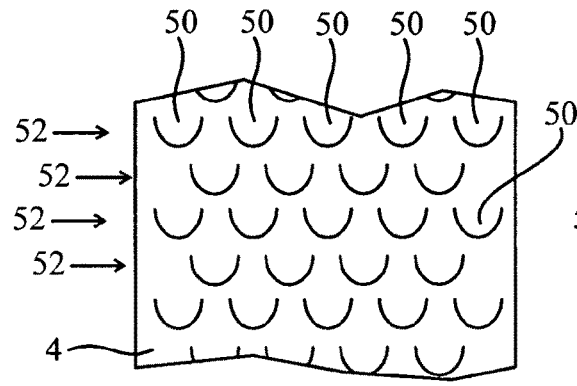
Figure 13:
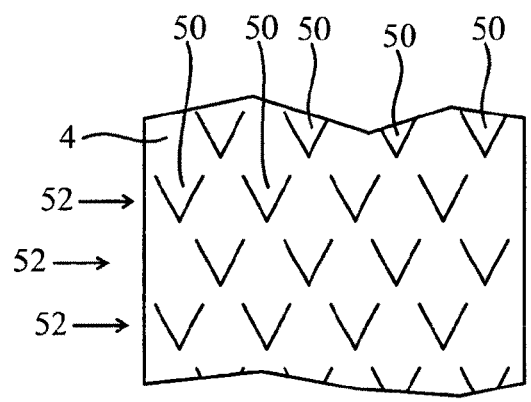
Figure 14:
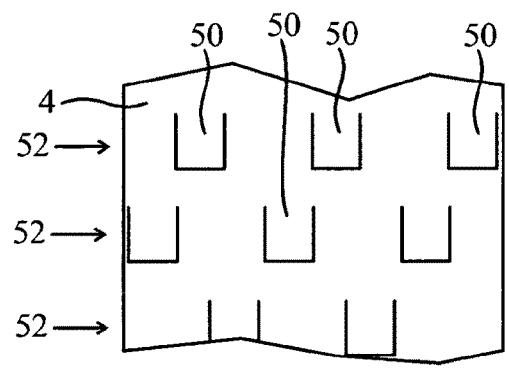

FIG. 10 shows a partial view of a system 2 according to further illustrative embodiments of the herein disclosed subject matter. According to an embodiment, scales 48, 50 are arranged on the first part 4 and the second part 6 in a way that they slide along each other during expansion, however get caught when reaching the desired diameter of the second state. The scales 48, 50 may exhibit a round from (FIG. 11, FIG. 12) like known from many fish scales, but also angular forms are possible. For instance the scales may be triangular (FIG. 13), quadrangular (FIG. 14) or polygonal (not shown).

Figure 12:
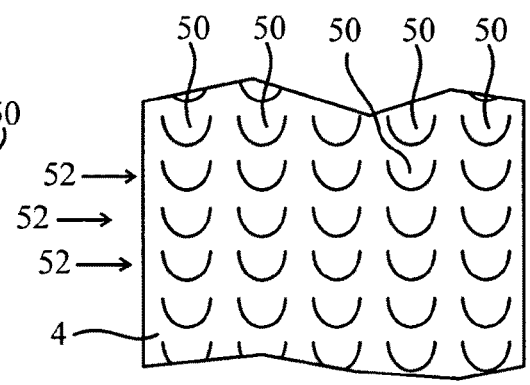

According to an embodiment (FIG. 11-FIG. 14), the scales 48, 50 may be lined up even. According to a further embodiment, the scales of successive rows may align (FIG. 12). According to other embodiments, the scales of successive rows are offset by a certain modulus, for example half of a scales width, or half of a horizontal scale distance (FIG. 11, FIG. 13, FIG. 14), whereby the horizontal scale distance is the distance of the scales in a row. According to a still further embodiment, the scales are disposed irregularly (not shown). According to a still further embodiment, on one part 4, 6 different forms of scales and arrangements are mixed. Although in FIG. 11 to FIG. 14 only the first part 4 is shown, it should be understood that also the second part 6 may be supplied with suitable scales 48 which can be identical to the scales 50 of the first part 4. According to another embodiment, the scales 48, 50 on the second part 6 and on the first part 4 are different. According to an embodiment, the scales are directed against each other as shown in FIG. 10, such that they block a decrease of the diameter of the system 2.

Figure 15:
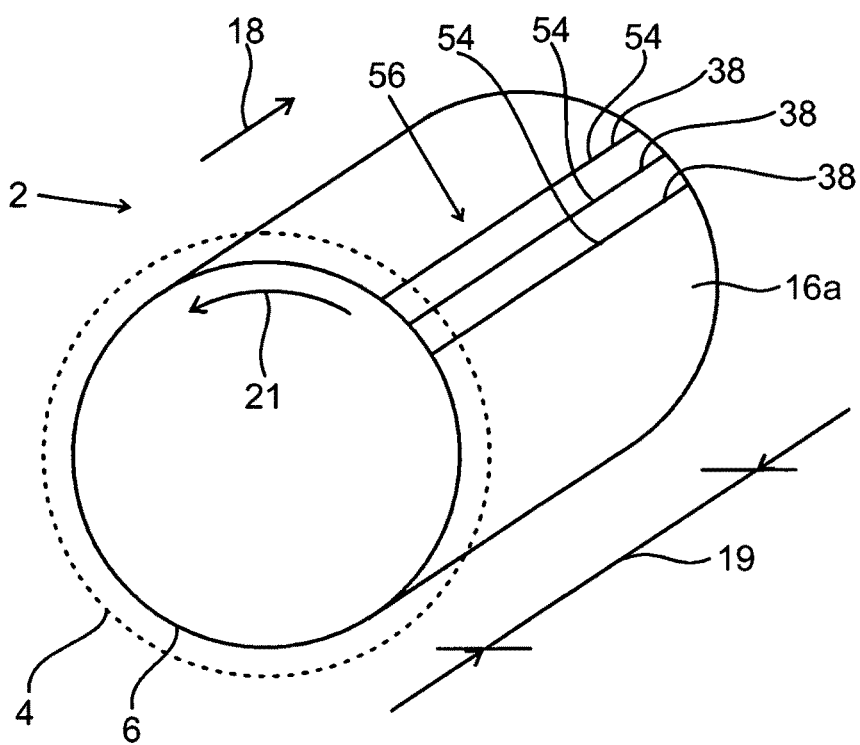
Figure 16:
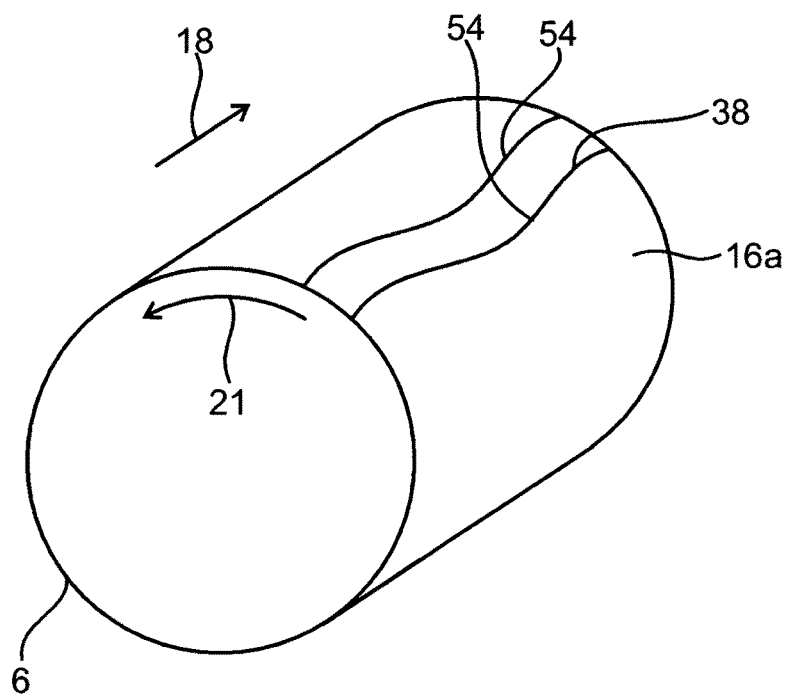

According to an embodiment one single fixation element, for example a first fixation element 36 or a second fixation element 38, can not only act locally, but can extend as an edge 54 running in longitudinal direction 18 of the system 2, for instance over part of the entire length 19 of the system 2 or over the entire length 19 of the system 2. The edges 54 can run parallel to the longitudinal direction 18 of the tube system (FIG. 15) or in a fixed angle or rolling forms (FIG. 16), for example sinusoidal. According to an embodiment edges 54 are arranged over the entire perimeter of the system 2. According to other embodiments edges 54 are only arranged over one or more perimeter sections 56 as demonstrated in FIG. 15 and FIG. 16. For reasons of clarity, in FIG. 15 and FIG. 16 only the second part 6 is shown. In FIG. 15, the first part 4 radially arranged over the second part 6 is shown as dashed line.

The edges 54 may for example be supplied with bumps 58 or indentations 60, respectively, extending in peripheral direction as shown for example in FIG. 17, or may be saw tooth shaped as for example shown in FIG. 18. Further, the edges 54 can exhibit different forms which allow a fixation of the first part 4 and the second part 6 to each other. The bumps 58 or the indentations 60 at the edge 54 can be constructed with radial distance from the respective part 4, 6, on which the edge 54 is located.

FIG. 19 and FIG. 20 show in each case a partial view of the first part 4 and the second part 6, respectively, of a system 2 according to further illustrative embodiments of the herein disclosed subject matter. According to an embodiment, one of the first fixation elements 36 and the second fixation elements 38 consists of hooks and the other of eyes. That means, either on the first part 4 or on the second part 6, respectively, hooks are located and on the other, corresponding part 6, 4, eyes. Shown is an embodiment in which on the first part 4 eyes 62 are arranged and in which on the second part 6 hooks 64 are arranged. The hooks 64 and eyes 62 are arranged for sliding along each other during expansion of the system 2 into the second state, and for getting caught during a reverse movement. In that way the first part 4 and the second part 6 are fixed securely together. According to further embodiments the eyes 62 are located on the second part 6 and the hooks 64 are located on the first part 4.

Figure 21:
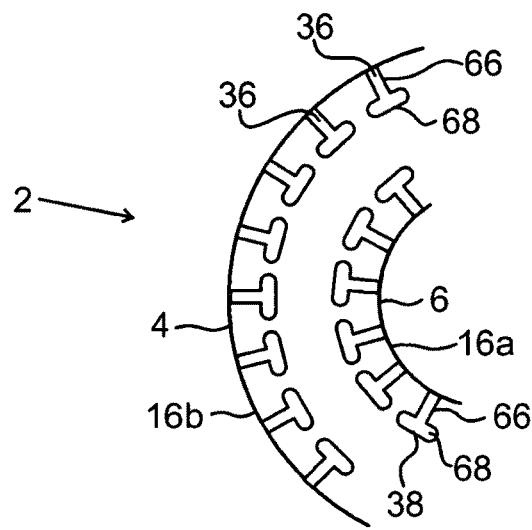

FIG. 21 shows a partial view of a system 2 according to further illustrative embodiments of the herein disclosed subject matter. According to an embodiment, the first fixation element 36 and the second fixation element 38 are fixed with a body portion 66 at the respective first part 4 or second part 6 and exhibit in direction of the respective other part 4, 6 a head portion 68, which has an enlarged diameter compared to the body portion 66. The fixation elements 36, 38 may be identical or may be different according to another embodiment. According to a further embodiment a plurality of first fixation elements 36 is distributed over the first part 4, whereby the first fixation elements have a first distance in peripheral direction 21. A plurality of second fixation elements 38 is distributed over the second part 6, whereby the second fixation elements 38 have a second distance from each other in peripheral direction. In this embodiment, the first distance and the second distance are chosen such that on reaching the predetermined second diameter, i.e. by reaching the second state 12 of the system 2, the position of the first fixation elements 36 aligns with the gaps in between the second fixation elements 38, and the first and the second fixation elements 36, 38 engage each other.

According to further embodiment, a blocking element (not shown), for example a foil, may be disposed between the first fixation elements 36 and the second fixation elements 38 which blocking element prohibits the snapping in of the first fixation elements 36 and the second fixation elements 38. On reaching the second state 12 of the system 2 the blocking element can be removed, whereon the first and the second fixation elements 36, 38 snap into each other.

According to an embodiment at least the radially outer part 4 is elastic and applies in the second state 12 a restoring force in direction of the first state 8, whereby a latch effect is provided in respective embodiments of the fixation elements 36, 38. It should be understood that usually the body tube applies onto the system 2 a restoring force in direction of the first state, i.e. in direction of the smaller diameter. Hence, depending on purpose, a restoring force applied by the first part 4 or by second part 6 may be omitted. For instance, at least one of the wall 16a, 16b or 16c, the first part 4 and the second part 6 may undergo a predominant plastic deformation during expansion into the second state 12. According to an embodiment, at least one wall element 16 and/or the first part 4 and/or the second part 6 may be flexible, i.e. be deformable, without substantial counterforce. For example, seen in peripheral direction, a wall element 16 may exhibit folds, which straighten upon an expansion.

According to intended use and/or place of installation of the system 2, a liquid, for example blood, flowing in the body tube may apply a pressure on the wall elements 16 of the system, which acts in direction of a larger diameter of the system 2.

It is obvious that with embodiments, in which two or more fixation elements 36, 38 are arranged along a peripheral direction, the fixation can be done in two or more steps. That means a system of that kind provides two or more second states in terms of the herein described subject matter.

According to a further embodiment, a fixation of the second state 12 of the system 2 comprises a mechanical fixation and an adhering (chemical, adhesive-) fixation. For instance at least one separate adhesive reservoir 28 may be arranged in the space in between the first part 4 and the second part 6 whereby additionally the first part 4 exhibits the first fixation element 36 and the second part 6 the second fixation element 38. At this the individual elements, in particular the adhesive reservoir 28, the first fixation element 36 and the second fixation element 38 can be designed according to the above mentioned embodiments.

According to an embodiment, fibers, e.g. fibers oriented in peripheral direction, may be placed in between the first part 4 and the second part 6. The fibers may for example be fastened to the first part 4, to the second part 6 or to the first part 4 and to the second part 6. The fibers can for example be carbon fibers, or consist of any other suitable material. These displace against each other during expansion and, in one embodiment, are glued in the second state, for example according to the herein described embodiments and examples. The forces exerted by the fibers may be pure mechanically or may be adhering forces such as van-der-Waals forces between the fibers on the first part and the fibers on the second part.

As mentioned above, the term adhesive generally includes any substance that causes adherence, such as glue or a substance that exerts van-der-Waals forces on surfaces. In this sense, the term adhesive includes fibers which adhere on surfaces such as a surface of the system 2, e.g. a surface of other fibers, a surface of the first part and/or the second part, or a surface of the body tube, etc. According to an illustrative embodiment, the diameter of the fibers is on micrometer scale. According to still another illustrative embodiment, the diameter of the fibers is on nanometer scale.

According to a further embodiment, the first part 4 and the second part 6 are fixated together in the second state only by friction forces. For instance the first part 4 and the second part 6 may be fixated in the second state by a friction force between the fibers, for example predominantly axial oriented fibers, on the first part and the second part.

According to an embodiment, between the first part and the second part a fleece tissue is arranged which stretches during expansion. By insertion or release of adhesive 30 between the first part 4 and the second part 6, as described herein, the tissue is fixed in the second state.

According to an embodiment, between the first part 4 and the second part 6 a tissue is arranged, which adopts a self stiffening structure in the second state.

Figure 22:
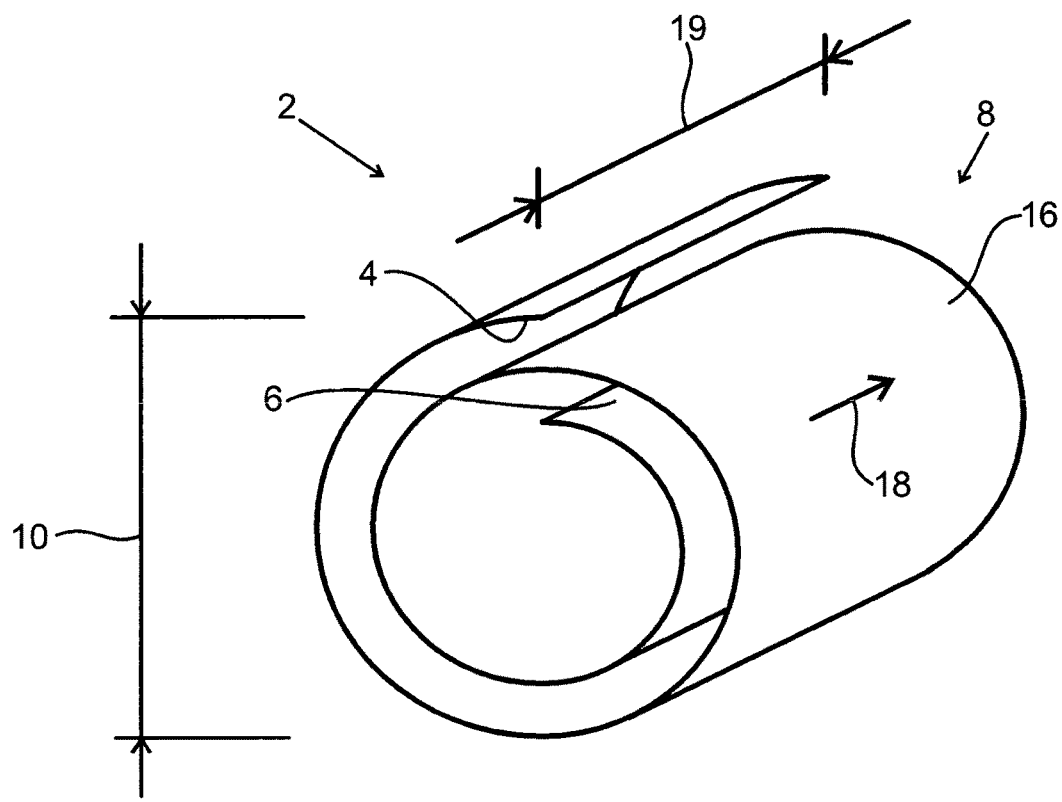
Figure 23:
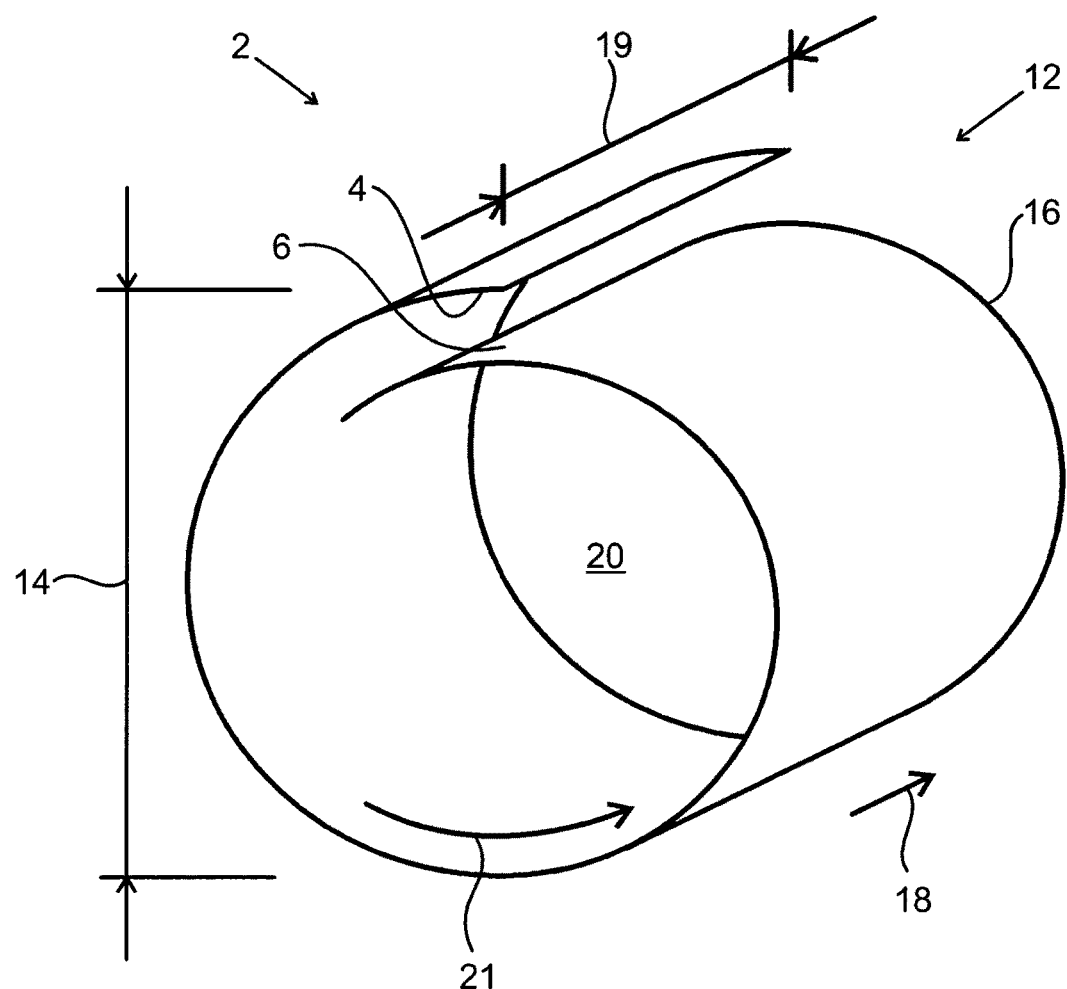

Besides embodiments in which the first part 4 and the second part 6 are arranged on separate, for example in peripheral direction hose like closed, wall elements 16a, 16b, 16c or are formed by the wall elements 16a, 16b, 16c, other embodiments of the herein disclosed subject matter comprise a wall element 16, which exhibits the first part 4 as well as the second part 6. FIG. 22 and FIG. 23 show such a radially expandable system 2 according to illustrative embodiments of the herein disclosed subject matter. The system 2 generally contains a first part 4 and a second part 6, whereby the system 2 exhibits a first diameter 10 in the first state 8 (FIG. 22). The system 2 is configured in a way that it can be brought into a second state 12 (FIG. 23) in which the system 2 exhibits a second diameter 14 which is larger than the first diameter 10. Further the system 2 is configured in a way such that the first part 4 and the second part 6 face each other in the second state 12 and are fixable to each other to keep the system 2 in the second state. According to an illustrative embodiment, the system exhibits a single wall element 16, which in the first state 8 is rolled up to the first diameter 10, and which is rolled up to the second diameter 14 in the second state 12. According to a further embodiment, the wall element 16 shows in peripheral direction two endings, from which a first ending forms the first part 4 and a second ending forms the second part 6, as shown in FIG. 22 and FIG. 23. According to an embodiment of the herein disclosed subject matter, a longitudinal extent 19 of the system 2 in the first state 8 and in the second state 12 is equal or almost equal.

In the system 2 as shown in FIG. 22 and FIG. 23, the first part 4 and the second part 6 overlap only in a perimeter section which is smaller than 360°. According to other embodiments the first part and the second part may overlap in a perimeter section which is larger than 360°, i.e. the number of plies of the wall 16 lying on top of each other in the first state, can add up three or more.

According to illustrative embodiments of the herein disclosed subject matter, of the system shown in FIG. 22 and FIG. 23 the first part 4 may exhibit a first fixation element 36 and the second part 6 may exhibit a second fixation element 38, whereby the first and the second fixation elements may be designed according to the herein described embodiments and examples.

The first part 4 and the second part 6 in FIG. 23 can be fixed together in any appropriate way or by any appropriate means, for example according to the above mentioned embodiments, as far as applicable. Further illustrative embodiments of the herein disclosed subject matter can be based on the system as described in FIG. 22 and FIG. 23 and further can contain criteria of the herein described embodiments and examples. Some of these embodiments are exemplarily shown in the following. Vice versa, criteria of consecutively described embodiments may also be combined with the preceding described embodiments.

FIG. 24 shows a system 2 according to further illustrative embodiments of the herein disclosed subject matter. The system 2 of FIG. 24 is based on the system of FIG. 23. Additionally the system exhibits an adhesive 30 which is directly applied on at least one of the first part 4 and the second part 6, for example on the second part 6 as shown in FIG. 24. The adhesive 30 can be configured as described herein in embodiments and examples. For instance the adhesive can be covered by a cover 32, to avoid a reaction with body liquids of the creature. The cover can exhibit a tear-off element 34 as described.

FIG. 25 shows a system 2 according to further illustrative embodiments of the herein disclosed subject matter. Unlike the system 2 in FIG. 24, the adhesive is not directly applied on at least one of the first part 4 or the second part 6, but located in at least one adhesive reservoir 28, which for example is applied at least to one of the first part 4 and the second part 6. The adhesive reservoir 28 can be fixed on the respective part 4, 6, or can be spatially fixed in regard to the respective part 4, 6, for example by a detaining device, for example a net. Also the adhesive reservoir 28 can exhibit a tear-off element 34 as described.

FIG. 26 shows a system 2 according to further illustrative embodiments of the herein disclosed subject matter. Unlike to FIG. 25 the adhesive is applied on a radially outer surface 39 of the system 2, which allows gluing of the system 2 with the respective body tube, in which the system 2 is inserted. According to an embodiment of the herein disclosed subject matter, the first part 4 and the second part 6 are solely fixed relative to each other by gluing the first part 4 and the second part 6 with the respective body tube. To this end, also the second part 6 can exhibit an adhesive 30, for example in form of a adhesive reservoir 28 or directly applied to the second part 6.

An embodiment of the herein disclosed subject matter allows the adhering of the first part 4 with the second part 6 as well as the adhering of one of the two parts, for example of the second part, with the body tube of the creature in which the system 2 is placed. For instance the positioning and/or the release of the adhesive 30 can take place such that adhesive 30 is deposed on a radially outer perimeter section, i.e. an outer surface of the system or is placed on a radially outer perimeter section of the system 2 which forms an outer surface in the second state of the system.

For instance by a further expansion of the system 2 as shown in FIG. 24, a perimeter section 31 carrying adhesive 30 is laid open. This is schematically shown in FIG. 27.

Figure 28:
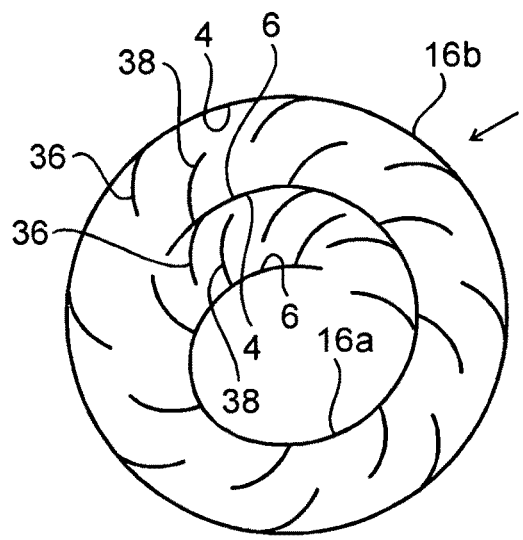

FIG. 28 shows a system 2 according to further illustrative embodiments of the herein disclosed subject matter. According to an embodiment, the system comprises at least one inner wall element 16a which is placed radially inside an outer wall element 16b and is open, i.e. not hose like closed in peripheral direction, as shown in FIG. 28. In other words, the system 2 in FIG. 28 comprises features of the system 2 as shown in FIG. 1 and FIG. 2 or FIG. 28, respectively, as well as features of the system 2 as shown in FIG. 22 and FIG. 23. FIG. 28 demonstrates the transferability of features of one embodiment of the herein disclosed subject matter to another embodiment.

Figure 29:
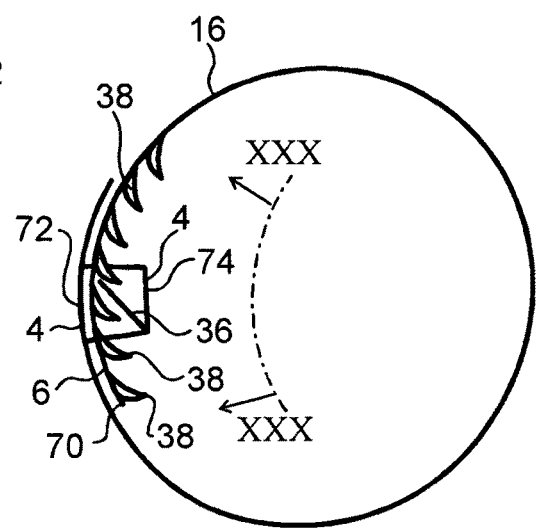
Figure 30:
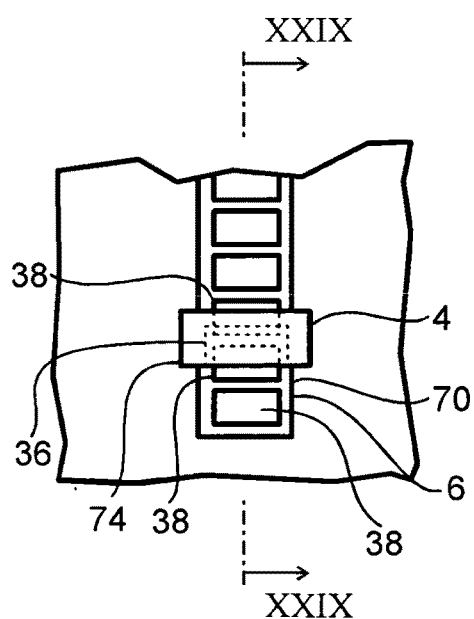

FIG. 29 shows a sectional view of a system 2 according to further illustrative embodiments of the herein disclosed subject matter. According to an embodiment, the second part 6 exhibits at least one ear 70, whereby in the second state 12, the first part 4 clasps the at least one ear 70 from two sides. According to an embodiment, the first part 4 may be provided for clasping the ear 70 already in the first state 8 from two sides. According to an embodiment, the first part 4 comprises at least one first fixation element 36 and the second part 6 comprises at least one second fixation element 38. FIG. 30 shows the first part 4 of FIG. 29 in top view, with the second part 6 plugged in the first part 4. The first part 4 is formed by a wall section 72 of the wall 16 and a bar 74, whereby the bar 74 extends at a distance over the wall section 72 and thus enables the through insertion of the ear 70 between wall section 72 and bar 74. According to an embodiment, at least one first fixation element 36 is placed on the bar 74. According to other embodiments the at least one first fixation element 36 can be placed on the wall section 72. According to further embodiments first fixation elements 36 are placed on the bar 74 and on the wall section 72.

As it appears in FIG. 29 and FIG. 30, according to an embodiment, the first fixation element 36 is formed by a snap-in pin and the second fixation element by a longitudinal profile along the ear 70. Hence, the first fixation element 36 and the second fixation element 38 of FIG. 29 and FIG. 30 work according to a snap-in principle, which is similar to the one of known cable straps. As it is apparent from FIG. 29 and FIG. 30, the system 2 shown herein can easily be enlarged to a desired diameter, whereby decreasing the diameter is impossible due to the snap-in effect of the first and second fixation elements 36, 38.

Figure 31:
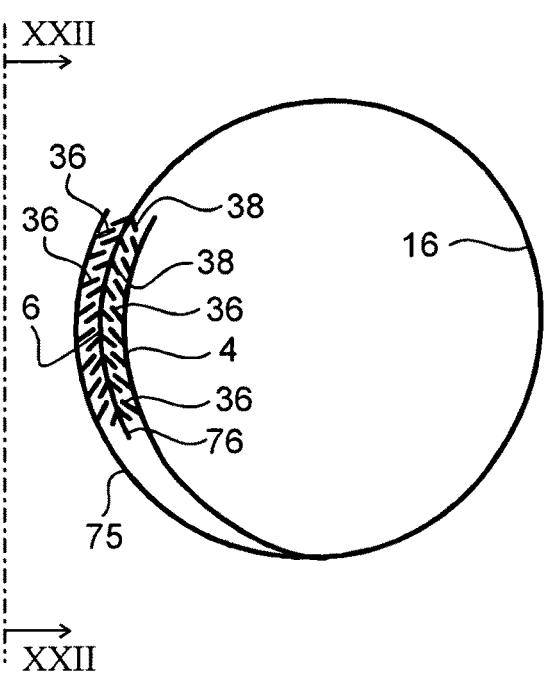

FIG. 31 shows a sectional view of a system 2 according to further illustrative embodiments of the herein disclosed subject matter. According to an illustrative embodiment, the first part 4 is build by at least one pocket 75 and the second part 6 exhibits at least one ear 76 which can be plugged into the ear 76 of the first part 4. According to an embodiment, the ear 76 of the second part 6 is clasped by the pocket 75 of the first part 4 from at least two sides. FIG. 32 shows the system 2 from FIG. 31 in side view along line XXII. Vice versa FIG. 31 shows the system 2 along intersection line XXI.

According to an embodiment, at least one first fixation element 36 is placed in the pocket 75 and the ear 76 exhibits at least one second fixation element 38, whereby the at least one first fixation element 36 and the at least one second fixation element 38 fix the first part 4 and the second part 6 in the second state 12 together. According to an embodiment, two or more ears 76 can be distributed over the longitudinal extension 19 of the system 2, as shown in FIG. 32. According to an embodiment the number of pockets 74 is equal to the number of ears 76. According to other embodiments the number of pockets 74 and the number of ears 76 can be different. According to an embodiment, the first part 4 extends over the whole longitudinal extension 19 of the system 2, as demonstrated exemplary in FIG. 32. According to a further embodiment, the second part 6 extends over the whole longitudinal extension of the system 2, as shown exemplary in FIG. 32.

FIG. 33 shows a part of a system 2 according to further illustrative embodiments of the herein disclosed subject matter. According to an embodiment, the system 2 includes telescope system 84, whereby the first part 4 is a first telescope part 78 and the second part 6 is a second telescope part 80, and whereby the first telescope part 78 and the second telescope part 80 are telescopically extendable to create the second state 12. The cross section of the telescope parts 78, 80 can have any arbitrary form adjusted to the intended use, for example round or rectangular. The number of first telescope parts 78 and the number of second telescope parts 80 can, according to an embodiment, be equal or can be different according to other embodiments. The first telescope part and the second telescope part can be curved, as shown in FIG. 33. According to an embodiment the first telescope part 78 and the second telescope part 80 can be at least be partly covered by a cover 82 (dashed lines in FIG. 33). The first telescope part 78 and the second telescope part 80 can be connected to the cover 82, for example by gluing. In another embodiment, a stop may be provided which limits the relative displacement of the first telescope part relative to the second telescope part. According to further embodiment, the cover can be an elastic cover, which is at least partially stretched over the first telescope part and the second telescope part. According to an embodiment, the elastic cover can be hose like closed in peripheral direction. According to a further embodiment the cover can be a wrap membrane.

The fixation of the first part 4 and the second part 6, that means the fixation of the telescope parts 78, 80 in the second state can be carried out according to the herein described embodiments and examples, for example by a adhesive 30 or by mechanical fixation devices 36, 38. The first part 4 and the second part 6 can be arranged on a wall element 16, for example on a wall element 16 of the system 2 forming the basis of FIG. 22 and FIG. 23 or on a wall element 16 of the system 2 forming the basis of FIGS. 1 and 2 or be build by the respective wall element 16.

FIG. 34 shows a part of a system 2 according to illustrative embodiments of the herein disclosed subject matter. According to an embodiment, the first part 4 is formed by the first telescope part 78 and the second part 6 is formed by the second telescope part 80. According to a further illustrative embodiment of the herein disclosed subject matter the system 2 contains a spreader device 84 which can be activated to keep the first part and the second part relative to each other in the second state. According to further illustrative embodiments, the first part 4 and the second part 6 are located opposite each other and angled in peripheral direction so that a force pressing both parts 4, 6 apart spreads the system, i.e. presses in direction of the second state. The force pressing apart the first part 4 and the second part 6 can be applied by any spreader element 86, for example by mechanical elements or chemical elements, e.g. a foamable material as shown in FIG. 34. In this sense the first part 4, the second part 6 and the spreader element 86 in the form of the foamable material form the spreader device 84.

According to illustrative embodiments, the activation of the foamable material can be carried out analog to the activation respectively release of the adhesive 30, as described herein. According to illustrative embodiments, the activation can be carried out by external effects like for example ultra sound, microwaves etc. The fixation in the second state can additionally to the chemical fixation by the foamable material and possibly additionally to further chemical fixation also be performed mechanically. The telescope system 84 can have a round cross section, but can also be oval or angular, for example rectangular. Along the longitudinal direction 18 of the system 2 two or more telescope systems 84 can be located. The telescope systems can be lined up along the longitudinal direction of the system with or without spaces. According to an embodiment, the telescope systems are interlinked, so that the telescope movement of the first telescope part 78 and the second telescope part 80 happen synchronously. The connection of two telescope systems 84 can be carried out in any suitable way, for example by adhering. According to a further embodiment, the system 2 exhibits only one telescope system 84. For instance the single telescope system 84 can extend over the whole length 19 of the system 2.

According to an illustrative embodiment, the system 2 contains a spreader device 84 which can be activated to move the first part and the second part into the second state. For instance a suitable foamable material can raise sufficient spreader force to bring the system 2 of FIG. 34 in a body tube, potentially yet against the resistance of a narrowing of the body tube, into the second state. According to an embodiment the foamable material is suitable to maintain the second state, for example by hardening, polymerization etc.

According to an embodiment the spreader device 84 comprises or consists of a suitable spreader element 86, for example a mechanical element which changes its shape depending on a temperature of the spreader element. An example of a spreader device of this kind is a memory shape metal element, for example of a nickel-titanium (NiTi) alloy, or a bimetal element.

The general design of the system 2 in the second state can have various shapes, for example according to illustrative embodiments of the subject matter disclosed herein.

Figure 35:
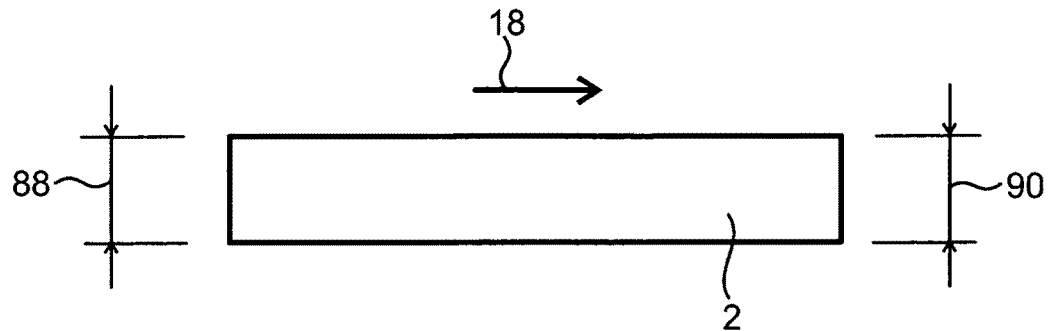
Figure 36:
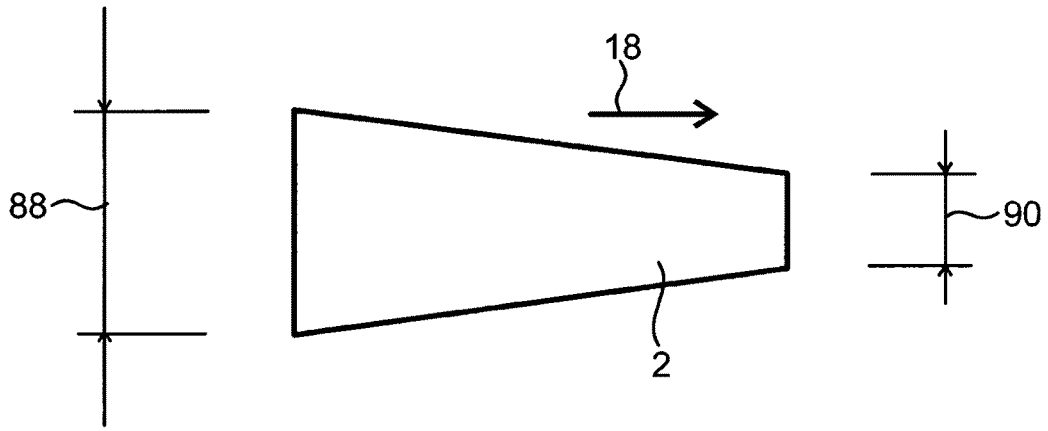
Figure 37:
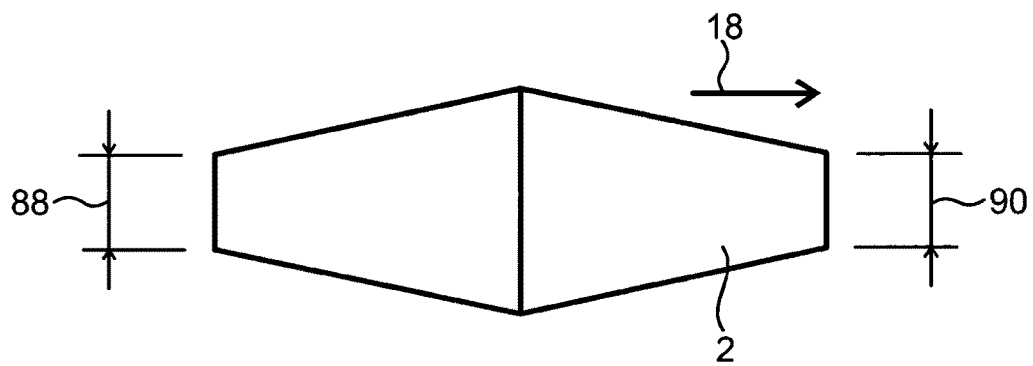
Figure 38:
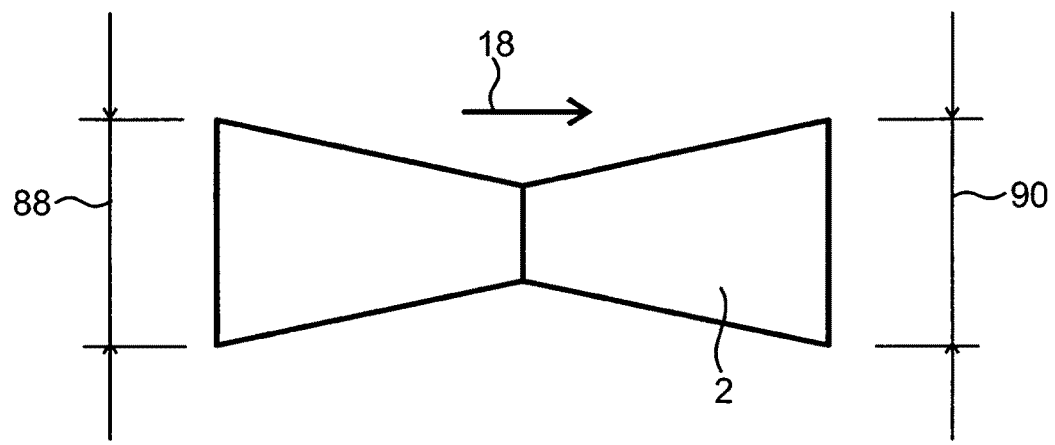
Figure 39:
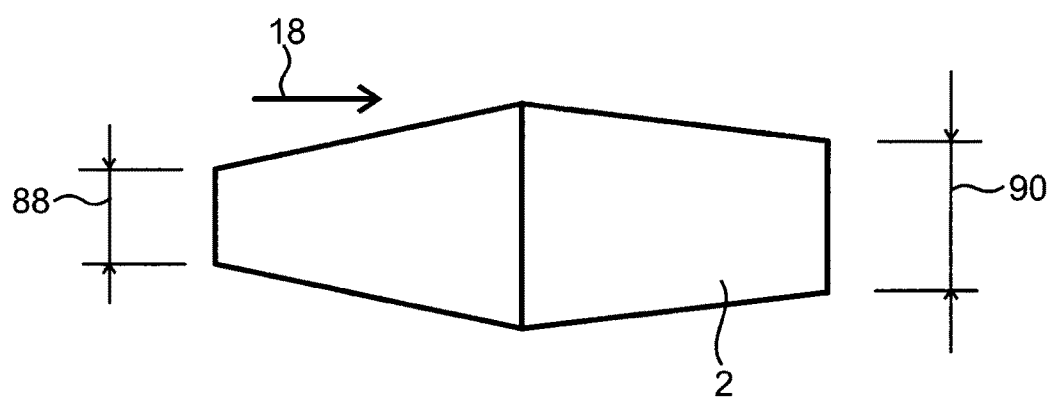

FIG. 35 shows a top view of a system 2 according to illustrative embodiments of the herein disclosed subject matter, which is cylindrical with a constant outer diameter 88, 90 in longitudinal direction 18 of the system 2. According to other embodiments the system 2 exhibits an outer diameter varying in longitudinal direction. For instance the system 2 can exhibit a conical shape (FIG. 36), a dual conical shape (FIG. 37) or an inverse dual conical shape (FIG. 38 and FIG. 39). Generally, the outer front end diameters 88, 90 of the system 2 can either be of same size (FIG. 35, FIG. 37, FIG. 38) or of different size (FIG. 36, FIG. 39). An outer diameter of the system 2 varying in longitudinal direction 18 has the advantage, that the system possibly has less tendency to slip in the body tube compared to a system with constant outer diameter.

Figure 40:
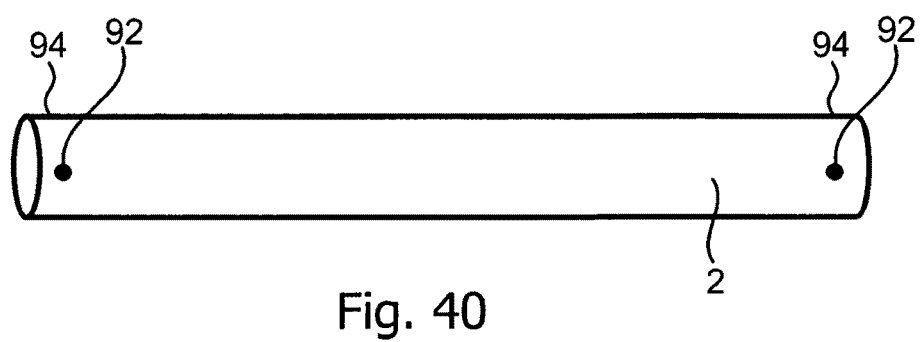

FIG. 40 shows a system 2 according to illustrative embodiments of the herein disclosed subject matter. According to an illustrative embodiment the system 2 exhibits at least one marker 92, which is visible in imaging systems. For example an imaging system can be a method capable of displaying a part of the inside of the body of a creature, for example a x-ray method, a computer tomography method, a magnetic resonance tomography method, a 2D/3D picture in which an in advance taken 3-dimensional picture of for example a body tube is overlaid by a real-time fluoroscopy. The marker 92 serves to visualize the position of the system 2. This is necessary if the system 2 consists of a material which is transparent for the imaging system, for example of plastic. In that case, the system 2 without marker can not or only poorly be seen with common imaging methods, during the insertion into the body tube as well as afterwards.

The marker 92 can be build of metal, or of any other suitable material, which gives a sufficient contrast in at least one of the imaging methods. The marker 92 can be for example point- or ring-shaped or can have any other shape. Marker 92 can be arranged at an arbitrarily chosen place of the system 2. For instance they can be located close to both front ends 94 of the system 2. According to a further embodiment at least one marker 92 can be placed at one front end 94.

By suitable attachments of the markers, cavities and vents in the system 2 can be labeled. By this, for example vascular outlets can be marked. By suitable choice of different shapes of the markers the user may be able to get an idea of the three dimensional circumstances even when having a two dimensional view.

Figure 41:
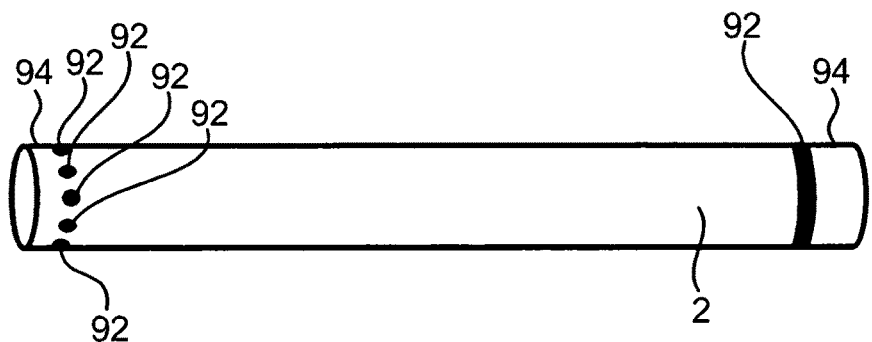
Figure 42:
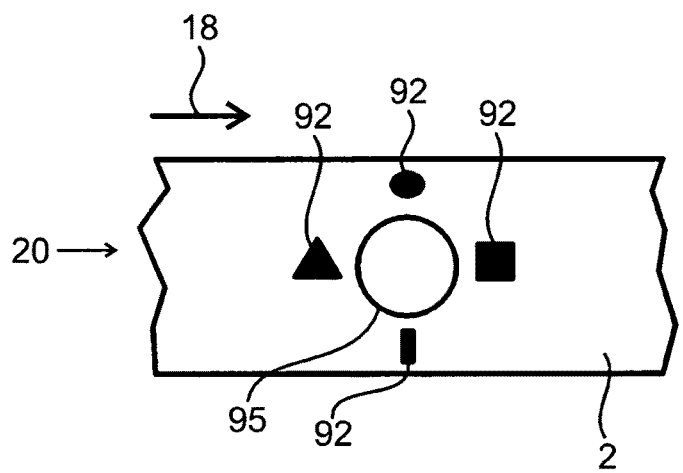

According to a further embodiment, the at least one marker 92 exhibits a configuration, which clearly defines its spatial orientation, as realized in the system 2 demonstrated in FIG. 41 and FIG. 42. Thus the marker allows a three dimensional determination of the position of the system 2.

FIG. 42 shows a system 2 according to further illustrative embodiments of the herein disclosed subject matter. According to an embodiment the system in the second state 12 exhibits a passage way 20 extending in a longitudinal direction 18 through the system and exhibits at least one opening 95 to the passage way 20. According to an embodiment the opening is marked by at least one marker 92. An opening can be necessary in case the system 2 extends over a vascular outlet.

An illustrative embodiment provides for the usage of a system 2, for instance a system according to the herein described embodiments and examples, for a function assistance of a body tube.

The system 2 and in particular the at least one wall element 16 can be of any material type. For instance the system 2 can be at least partly an extrudate. Further, the system 2 can be at least partly be made of a tissue. The tissue can for example be knitted, woven or binded. Further, the system 2 can be at least partly made of felt. Further, the system 2 can be at least partly made of a sheet. Further, the system 2 can be preformed tube like; in particular the system 2 can be at least in the first state be rolled up to a roll.

According to an embodiment the wall thickness of the wall element 16 is chosen depending on at least one of the following parameters:
  intended use of the inventive system, e.g. depending on the body tube in which the system is inserted;
  material of the wall element.

According to illustrative embodiments, the wall thickness can be between 10 nanometer (nm) and 2 millimeter (mm). According to further embodiments the wall thickness can be between 10 micrometer (um) and 500 micrometer (um). According to further embodiments the wall thickness can be between 20 micrometer (um) and 100 micrometer (um). It has to be emphasized that the herein disclosed subject matter is not limited to the denoted wall thicknesses and that depending on the real demands wall thicknesses can be chosen to be outside the denoted wall thicknesses.

According to an embodiment the wall element 16 is a flexible hull. If multiple wall elements 16 are arranged radially in one another, the individual wall elements can be constructed with lower stiffness, whereby in the second state the desired stiffness of the system 2 results from fixation of the individual, radially in each other arranged wall elements 16. According to an embodiment of the herein disclosed subject matter, the at least one wall element exhibits a stiffness, so that at least in the second state the system is dimensionally stable.

The system and in particular the at least one wall element can be made of any suitable material.

For instance suitable materials can be:
  plastics, in particular polymers like for example polyester, polyamides, polyurethanes, siliconelastomeres, polypropylene, polyethylene, polytetrafluorethylene, polyethyleneterephthalate, polycarbonate, polyvinylchloride, Polymethylacrylate, PGLA (polymer polyglycolic-lactic acid), as well as combinations from two or more of these polymers, or, as long as chemically feasible, alloys from two or more of these polymers.

Further the polymers can exhibit at least one metal as further component. According to illustrative embodiments, metals can for example contribute to a higher chemical and/or mechanical stability, breaking strength, or flexibility of the material.

Further the polymers can exhibit further organic and/or inorganic compounds as further components.

The polymers can be used together with the further components as mixture. Further the polymers can be used with the further components as composite material.

According to illustrative embodiments, the system can be constructed from biocompatible materials. Further, the system can be coated by a biocompatible material.

Figures 43, 44:
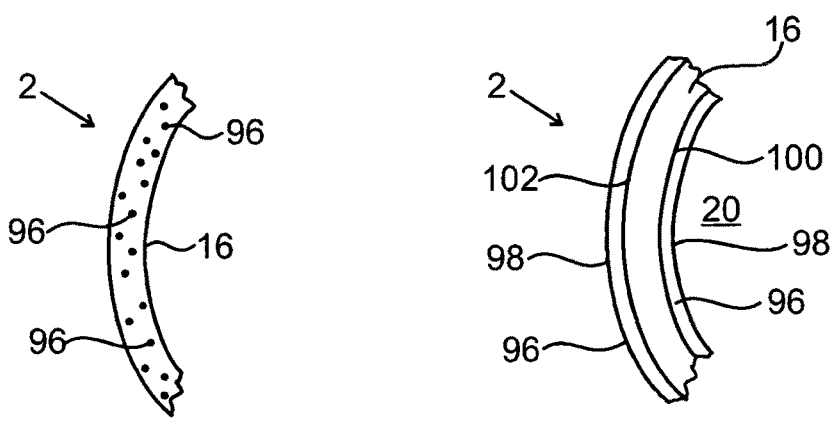

According to illustrative embodiments, the system can at least partly be constructed from a material which contains at least one medicament. For instance, with suitable polymers at least one medicament can be directly incorporated in the polymer. This is exemplarily demonstrated in FIG. 43, wherein the system 2 exhibits a wall element 16 made of a polymer, in which a medicament 96 is incorporated. According to further illustrative embodiments, the system 2 may be at least partially coated with a medicament 96. FIG. 44 shows a system 2 according to further illustrative embodiments of the herein disclosed subject matter. According to an embodiment, a wall element 16 can be coated with a coating 98 which contains a medicament 96. The coating 98 or the medicament 96, respectively, can be arranged on a inner surface 100 of the system 2 facing the passage way 20 of the wall element 16, or can be arranged on an outer surface 102 of the wall element 16 facing away the inner surface 100, or can be arranged on the inner surface 100 and the outer surface 102, as demonstrated in FIG. 34. According to an illustrative embodiment, the surface coating is made of a biocompatible material.

Figure 45:
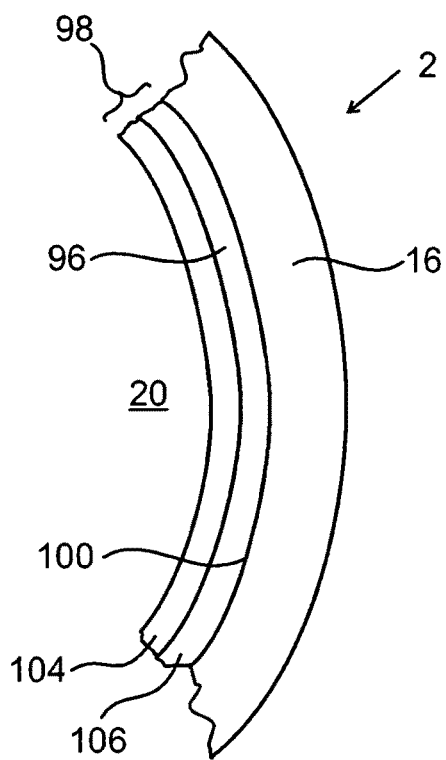

FIG. 45 shows a partial sectional view of a system 2 according to illustrative embodiments of the herein disclosed subject matter. According to an illustrative embodiment, the system 2 can at least partly exhibit two more layers, wherein between the layers at least one medicament 96 is stored. For instance, the system 2 can exhibit a wall element 16 coated with a coating 98 which comprises a biocompatible layer 104 and medicament layer 106. The medicament layer comprises at least one medicament 96 or consists of at least one medicament 96. The medicament layer 106 is placed in between the wall element 16 and the biocompatible layer 104. The medicament layer 106 can be a continuous layer. According to a further embodiment, the medicament layer 106 can consist of at least one medicament 96, which is arranged punctual in between the biocompatible layer 104 and the wall element 16.

According to an illustrative embodiment, an outer surface as well as an inner surface of the system 2 form a closed and smooth surface. Thus the risk of injuries during expansion of the body tube can be avoided or at least reduced. A flaking and swimming away of plaques, which can be present on an inner surface of the body tube, can be avoided or at least be reduced. Contrary to conventional systems with grid like structures no body tissue can intrude into the passage way 20 and further grow there (restenosis). The smooth surface of the system 2 in the interior room of the body tube can let flow the liquid current without or with relatively marginal turbulences. Thus the inner diameter of the body tube as well as of the system 2 stays constant over a long period of time.

A further embodiment of a system 2 is characterized in that one or more of the wall elements 16 exhibit holes and/or passages. For instance one or more wall elements 16 can be build grid like. The size of these holes/passages can vary, also within the system 2. So, there can be for example on one or both ends of the system smaller or larger holes/passages, in the middle smaller ones. Is the system made up of an inner and an outer wall element 16 with holes/passages, the holes respectively passages can be arranged in a way that they lay on top of each other after expansion, thus making the system 2 porous between the wall of the body tube and the passage way 20. According to another embodiment, the holes respectively the passages can overlap. Holes or passages, respectively, enable contact between body liquid and wall of the body tube. Further, holes or passages, respectively, can enable a possibility of flow at junctions of the body tube. Further, holes/passages in the wall elements reduce the weight of the system 2.

According to further embodiments, at least one wall element can be holey, porous or sievelike. According to a further embodiment, at least one wall element can comprise a semi-permeable membrane or can be built of a semi-permeable membrane.

According to an embodiment, the system can exhibit a different structure on its inner surface facing the passage way than on its outer surface, which faces the body tube in the inserted state. For instance, the inner surface can be smooth and the outer surface be rough. The inner surface and the outer surface can be formed by the wall element itself or by a surface coating of the wall element.

According to an embodiment, an inner wall element facing the passage way can exhibit a different structure, for example a different punching, than an outer wall element which faces the body tube in the inserted state.

Figure 46:
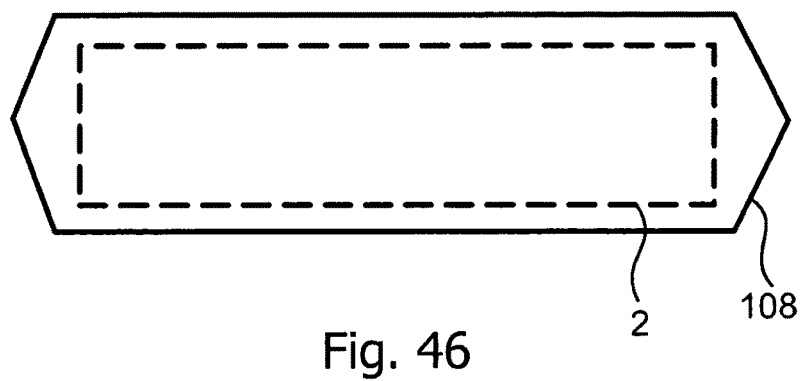

FIG. 46 shows a system 2 according to further embodiments of the subject matter described herein. According to an embodiment, the system 2 is covered by a protective shielding 108. According to a further embodiment, the protective shielding 108 is provided for remaining on the system 2 during insertion into the body tube. According to an embodiment the protective shielding 108 fixes the system 2 on an insertion device, with which the system can be brought to a desired location in the respective body tube. According to a further embodiment the system 2 contains a tissue adhesive 30, e.g. cyanoacrylate, and the protective shielding 108 prevents a contact of the tissue adhesive 30 with a body liquid prior of reaching the desired location in the body tube.

According to a further embodiment, the protective shielding 108 is designed to enable contact between the tissue adhesive 30 and the body tube during expansion of the system 2. For instance, the protective shielding can be designed to rip during expansion. According to a further illustrative embodiment, the protective shielding can be designed to become permeable for body liquids in the second state. For instance, the protective shielding can be designed to have passages in the second state, for example in form of pores, which are permeable for body liquids.

According to a further embodiment, the protective shielding 108 is designed to be removed from the system 2 before reaching the second state, for example before the expansion. The removing of the protective shielding 108 from the system 2 can be done for example with a peel off device arranged at the insertion device.

Figure 47:
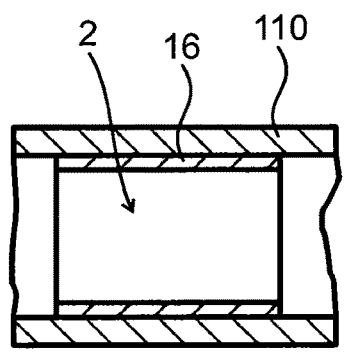
FIG. 47 shows a sectional view of a radially expandable system according to illustrative embodiments in a body tube.

FIG. 47 shows exemplarily a longitudinal cut of a radially expandable system 2 according to herein described embodiments and examples in a body tube 110. For instance the radially expandable system 2 can be brought into the body tube 110 with a conventional insertion system.

Some of the before described embodiments and examples have been described with reference to a system of a first type, in which a first wall element 16 exhibits the first part 4, and a second wall element 16b exhibits the second part 6 (see for example FIG. 1, FIG. 2), whereas other embodiments and examples have been described with reference to a system of a second type, in which the first part 4 and the second part 6 are formed on or by a single wall element 16. It should be understood that the embodiments and examples of the system of the first type can be combined with embodiments and examples of a system of the second type unless specifically excluded.

In summary, a technique is presented herein which provides a radially expandable system for insertion in body tubes, for example in form of a body tube insert, which is kept, by fixation of a first part and a second part relative to each other, in a second state in which the system exhibits a larger diameter compared to a first state. A first diameter in the first state can be small enough to allow insertion of the radially expandable system into a body tube. Through the radially expandable system, a body tube, for example a vein, can be assisted in its function. For instance the body tube can be kept open by the radially expandable system or a weak point of the body tube, for example an aneurysm can be at least partly relieved or bridged, whereby a deterioration of the state of the body tube can be avoided. According to an embodiment a radially expandable system can exhibit at least one first part and at least one second part, whereby a respective one of the at least one first part and a respective one of the at least one second part lay opposite each other in the second state and are fixable relative to each other to keep the system in the second state.

The first part and the second part can be arranged on or formed of one single wall element or two different wall elements. According to an embodiment, at least one wall element is hose like in the second state. For instance the respective wall element can be hose-like closed. Further, the respective wall element can be rolled in a hose-like form, for example from a piece of sheet, e.g. a plastic sheet or a metal sheet. For closure of the hose-like wall element in peripheral direction, overlapping portion of the rolled sheet may be adhered together. However, the hose-like closed wall element may be formed by any other suitable method, e.g. by extruding. According to a further embodiment, two or more wall elements add up in a peripheral direction to a hose like system in the second state. According to another embodiment, two or more wall elements are arranged radially in each other and are fixable relative to each other, for example fixable together, by respective first parts and second parts.

According to illustrative embodiments, at least one of the first part or of the second part can exhibit one or more fixation elements, e.g. at least one of adhesive fixation elements and mechanical fixation elements. Chemical fixation elements for example include respective adhesives or adhesive reservoirs. Mechanical fixatives can include fibers, hooks, hooks and ears, scales, edges, knobs, latch elements etc., whereby a radially expandable system may exhibit one of the herein described fixation elements or two or more of the herein described fixation elements. Further, the system can exhibit markers, which are visible in imaging methods, for example visible in x-ray- or tomography methods. The markers can be arranged and/or configured for determination of a spatial orientation of the system. According to an embodiment, the radially expandable system can be brought into the body tube be means of a conventional insertion system. Further, the radially expandable system can be brought into the body tube by a specially constructed insertion system which accommodates for the characteristics of the respective embodiment of a radially expandable system.

A first part or a second part of the herein described subject matter may for example denote a wall element, a part of a wall element, a surface of a wall element, or a portion of a wall element. "Expanding" in the meaning of the herein described subject matter describes the enlargement of the diameter of the system 2 and comprises the bringing of the system in the second state. According to an illustrative embodiment, the expansion may involve a dilation of parts of the system. For instance such a system can be of the type of system shown in FIG. 1. According to other illustrative embodiments, the expansion can take place without material dilation. For example, such a system can be of the type of the system shown in FIG. 18.

In illustrative embodiments of the herein disclosed subject matter the length of the radially expandable system in the first state as well as in different diameters in the second state is more or less equal. The diameter in the second state stays at the adjusted value after the expansion, i.e. there is no post-shrinking.

The expressions used in the description are not limited to an interpretation in the light of an embodiment or an example. For instance "ripping" or "getting permeable" always includes, but is not limited to, in the meaning of the herein described subject matter, ripping at a predetermined breaking point, getting permeable by external impact, etc. An external impact in this meaning includes, but is not limited to, for example, contactless energy like for example a laser beam or ultra sound, or mechanical impact like for example a sharp object. The term "comprising" does not exclude other steps or elements. The term "one" does not exclude a plural unless specified as "single one". The terms "exhibit" or "comprising" also include "consisting of". Even if it is not explicitly mentioned, elements which are described with regard to different embodiments may be combined. Reference symbols in the claims are only provided for illustrative purposes with reference to illustrative embodiments and shall not be interpreted in a restrictive manner.

Further modifications and variations of the present invention will become apparent to a skilled person in view of this description. Accordingly, this description is to be construed as illustrative only and is intended for the purpose of teaching a person skilled in the art the general manner of carrying out the present invention. It is to be understood that the forms of the herein disclosed subject matter shown and described herein are to be taken as the presently preferred embodiments.

The invention claimed is:

1. Radially expandable system for the insertion in a body tube of a creature, the system comprising:
    a first wall element defining a first tubular part;
    a second wall element defining a second tubular part, the first wall element arranged radially outside the second wall element, the first wall element forming an inward facing surface, the second wall element forming an outward facing surface opposite the inward facing surface, the inward facing surface and the outward facing surface defining a space therebetween; and
    an adhesive arranged in an enclosed reservoir located in the space between the inward facing surface and the outward facing surface;
    wherein the system exhibits in a first state a first diameter;
    the system is configured to be expandable to a second state in which the system exhibits a second diameter which is larger than the first diameter, in the second state the first tubular part and the second tubular part are fixable relative to each other by said adhesive released from said enclosed reservoir in order to keep the system in the second state.

2. System according to claim 1, wherein the enclosed reservoir is formed from a non-elastic material that rips as the system expands to the second state.

3. System according to claim 1, wherein the enclosed reservoir is opened by an external impact.

4. System according to claim 3, wherein said adhesive is arranged on at least one of the first part and the second part.

5. System according claim 1, further comprising a cover arranged in the first state to prohibit contact between the adhesive and body fluids, wherein in said second state said adhesive is uncoverable such that fixation is uncoupled from transition from the first state to the second state.

6. System according to claim 1, further comprising an adhesive disposed on said outward facing surface for adhering said outward facing surface in said second state to the body tube.

7. System according to claim 1, wherein the adhesive comprises a plurality of fibers.

8. System according to claim 1, wherein adhering forces exerted by said adhesive are Van-der-Waals forces.

9. System according to claim 1, wherein
    the first tubular part exhibits at least one first fixation element; and
    the second tubular part exhibits at least one second fixation element, wherein
    the at least one first fixation element and the at least one second fixation element fix together the first tubular part and the second tubular part in the second state.

10. System according to claim 1, comprising a spreader device which is activatable to move the first part and the second part relative to each other into the second state.

11. System according to claim 1, further comprising at least one marker being visible in an imaging method.

12. System according to claim 1, wherein said adhesive is a tissue adhesive.

13. System according to claim 1 for use in assistance of the function of a body tube.

14. Radially expandable system for the insertion in a body tube of a creature, the system comprising:
    a first wall element defining a first tubular part;
    a second wall element defining a second tubular part opposed to the first wall element, the first wall element and the second wall element defining a space, the first wall element arranged radially outside the second wall element with both the first wall element and the second wall element arranged in a tubular manner; and
    an adhesive enclosed in a reservoir arranged between the respective wall elements of the first tubular part and the second tubular part in the space;
    wherein the system exhibits in a first state a first diameter;
    the system is configured to be expandable to a second state in which the system exhibits a second diameter which is larger than the first diameter;
    in the second state the first tubular part and the second tubular part are fixable relative to each other by said adhesive released from said enclosed reservoir in order to keep the system in the second state.

* * * * *